US012611389B1

(12) United States Patent

Martin

(10) Patent No.:  US 12,611,389 B1

(45) Date of Patent:  Apr. 28, 2026

(54) COMPOSITIONS AND METHODS TO REDUCE OR ELIMINATE NASAL BIOFILMS AND MUCUS BARRIERS ALLOWING SODIUM PYRUVATE TO INCREASE THE SYNTHESIS OF NITRIC OXIDE AND ELIMINATE NASAL INFECTIONS AND THEIR TOXINS THAT CAUSE LUNG, NERVE AND BRAIN DAMAGE

(71) Applicant: Cellular Sciences, Inc., Flemington, NJ (US)

(72) Inventor: Alain Martin, Flemington, NJ (US)

(73) Assignee: Cellular Sciences, Inc., Flemington, NJ (US)

( * ) Notice: Subject to any disclaimer, the term of this patent is extended or adjusted under 35 U.S.C. 154(b) by 0 days.

(21) Appl. No.: 19/301,639

(22) Filed: Aug. 15, 2025

(51) Int. Cl.

| | |
|---|---|
| *A61K 31/19* | (2006.01) |
| *A61K 47/02* | (2006.01) |
| *A61K 47/10* | (2017.01) |
| *A61K 47/18* | (2017.01) |
| *A61P 29/00* | (2006.01) |
| *A61P 37/08* | (2006.01) |

(52) U.S. Cl.

CPC .............. *A61K 31/19* (2013.01); *A61K 47/02* (2013.01); *A61K 47/10* (2013.01); *A61K 47/186* (2013.01); *A61P 29/00* (2018.01); *A61P 37/08* (2018.01)

(58) Field of Classification Search

CPC ...................................................... A61K 31/19

See application file for complete search history.

(56) References Cited

U.S. PATENT DOCUMENTS

| | | | |
|---|---|---|---|
| 3,920,835 | A | 11/1975 | Van Scott et al. |
| 3,984,566 | A | 10/1976 | Van Scott et al. |
| 3,988,470 | A | 10/1976 | Van Scott et al. |
| 4,158,057 | A | 6/1979 | Stanko |
| 4,234,599 | A | 11/1980 | Van Scott et al. |
| 4,351,835 | A | 9/1982 | Stanko |
| 4,415,576 | A | 11/1983 | Stanko |
| 4,645,764 | A | 2/1987 | Stanko |
| 5,210,098 | A | 5/1993 | Nath |
| 5,798,388 | A | 8/1998 | Katz |
| 5,939,459 | A | 8/1999 | Katz |
| 5,952,384 | A | 9/1999 | Katz |
| 6,623,723 | B2 | 9/2003 | Katz |
| 6,689,810 | B2 | 2/2004 | Martin |
| 8,076,373 | B2 | 12/2011 | Martin |
| 8,114,907 | B2 | 2/2012 | Martin |
| 10,813,893 | B2 | 10/2020 | Martin |
| 11,311,505 | B2 | 4/2022 | Martin |
| 11,628,186 | B2 | 4/2023 | Martin |
| 2002/0006961 | A1 | 1/2002 | Katz et al. |

FOREIGN PATENT DOCUMENTS

| | | | |
|---|---|---|---|
| WO | WO 0069431 | * | 11/2000 |

* cited by examiner

*Primary Examiner* — Rei Tsang Shiao

(74) *Attorney, Agent, or Firm* — Wilkinson Law Office; Clinton H. Wilkinson

(57) ABSTRACT

Compositions and methods reduce and penetrate biofilms and mucus barriers to deliver pyruvate that increases synthesis of nitric oxide inhibiting replication and severity of bacterial, virus and fungal infections in lungs or nasal cavity, increase lung functions and reduce coughing reflex by reducing inflammatory cytokines that stimulate Vagus nerve coughing reflex and to eliminate bacterial toxins that cause brain diseases like Alzheimer's, and Parkinson's. It reduces symptoms, including hypoxemia, cytokine storm and lung fibrosis when biofilms are destroyed. Composition is sodium pyruvate; sodium chloride; benzalkonium chloride; alcohol selected from: ethanol, isopropanol, methyl alcohol or phenylethyl alcohol; and an aqueous carrier.

20 Claims, No Drawings

COMPOSITIONS AND METHODS TO REDUCE OR ELIMINATE NASAL BIOFILMS AND MUCUS BARRIERS ALLOWING SODIUM PYRUVATE TO INCREASE THE SYNTHESIS OF NITRIC OXIDE AND ELIMINATE NASAL INFECTIONS AND THEIR TOXINS THAT CAUSE LUNG, NERVE AND BRAIN DAMAGE

BACKGROUND OF INVENTION

Field of Invention

The present invention generally relates to compositions and to methods utilizing unique synergistic compositions that reduce, destroy and penetrate biofilms and mucus barriers to deliver drugs that increase the synthesis of nitric oxide that will inhibit the replication, spread, duration and severity of bacterial, virus and fungal ailments, in the lungs or nasal cavity and to increase all lung functions and reduce coughing caused by inflammatory cytokines and bacterial toxins that also cause brain diseases like Alzheimer's, and Parkinson's. The present invention is also a treatment method to reduce symptoms, including hypoxemia, the cytokine storm and lung fibrosis when biofilms are destroyed. The present invention is based on the discovery that pulmonary dysfunction, sinus and lung infections, characteristic of certain disease states, is attributable to the decrease in the synthesis of nasal nitric oxide caused by infections by organisms that produce biofilms and mucus barriers. Inflammatory pathways are upregulated in the nasal epithelium in 40-80% of patients with Pulmonary fibrosis, Idiopathic pulmonary fibrosis, Parkinsons, Alzheimer's and in patients with sinusitis, Cystic fibrosis the majority of which is caused by infections that produce biofilms and mucus barriers which is part of the etiology of the disease that affects all sinus and lung functions and increases inflammatory cytokines that stimulate the nasal nerves to increase the coughing reflex. The production of biofilms and mucus barriers reduces the efficacy of nasal and lung medications to penetrate the biofilm to effectively treat the disease state. This decrease in nasal nitric oxide increases duration and severity of the sinus and lung infections, which increases toxins that increase inflammatory cytokines, to reduce sinus and lung capacity and functions, increase lung fibrosis, and coughing reflex. These toxins can cross the blood brain barrier to destroy brain cells to product Alzheimer's and Parkinson's.

Description of Related Art

The following patents are representative of the field pertaining to the present invention:

U.S. Pat. No. 5,210,098 issued to Nath discloses a method to arrest or prevent acute kidney failure by administration of a non-toxic pyruvate salt to a patient in need of such treatment. The Nath invention provides a therapeutic method comprising administration of an amount of pyruvate salt to a patient experiencing, or in danger of, acute renal failure.

U.S. Pat. Nos. 3,920,835, 3,984,556, 3,988,470, and 4,234,599 all issued to Van Scott et al. disclose methods for treating acne, dandruff, and palmar keratosis, respectively, which consist of applying to the affected area a topical composition comprising from about 1% to about 20% of a lower aliphatic compound containing from two to six carbon atoms selected from the group consisting of alpha-hydroxy acids, alpha-ketoacids and esters thereof, and 3-hydroxybutryic acid in a pharmaceutically acceptable carrier. The aliphatic compounds include pyruvic acid and lactic acid.

U.S. Pat. Nos. 4,158,057, 4,351,835, 4,415,576, and 4,645,764, all issued to Stanko, disclose methods for preventing the accumulation of fat in the liver of a mammal due to the ingestion of alcohol, for controlling weight in a mammal, for inhibiting body fat while increasing protein concentration in a mammal, and for controlling the deposition of body fat in a living being, respectively.

U.S. Pat. Nos. 5,798,388, 5,939,459, 5,952,384, 6,623,723 and US-20020006961 A1, issued to Katz and Martin, the inventor herein, pertain to methods for treating inflammation in the lungs and compositions useful in the method. The method comprises contacting the mammalian cells participating in the inflammatory response with an inflammatory mediator. The inflammatory mediator is present in an amount capable of reducing the undesired inflammatory response and is an antioxidant. 20020006961 A1, issued to Katz and Martin, the inventor herein teaches the use of 0.65% sodium chloride with sodium pyruvate and the use of a preservative. This formula only used 0.01% benzalkonium chloride that did not include ethanol or a 0.9% sodium chloride deliver formula. This formula was not able to penetrate biofilms or mucus to deliver sodium pyruvate to enhance the synthesis of nasal nitric oxide. It was developed for patients with season allergies.

U.S. Pat. No. 6,689,810, issued to Martin, the inventor herein, discloses a therapeutic composition for treating pulmonary diseases states in mammals by altering indigenous in vivo levels of nitric oxide. The therapeutic composition consists of pyruvates, pyruvate precursors, alpha-keto acids having four or more carbon atoms, precursors of alpha-keto acids having four or more carbons, and the salts thereof. Martin also claimed that all salts of pyruvate were equal. The treatment with sodium pyruvate was designed for nebulizers taken orally through the mouth and the range of sodium pyruvate in saline was 0.001 mM to 0.5 mM. Nasal inhalation of sodium pyruvate at higher levels like 20 mM was not taught or practiced.

U.S. Pat. Nos. 8,076,373 and 8,114,907 Martin, the inventor herein, discloses a method for treating pulmonary disease state in mammals by up or down regulating in vivo levels of inflammatory agents (cytokines) in mammalian cells, in hypotonic saline formulas, with various alpha keto acid combinations.

United States Patent Application Publication No 10,813,893 B2 Martin, the inventor herein, discloses a composition and methods for the treatment and prevention of chronic hypoxemia and dyspnea. The therapeutic composition consists of sodium pyruvate in saline and must include compounds that work synergistically to enhance lung surfactants that will enhance alveoli functions. This patent never taught a method that allows sodium pyruvate to penetrate biofilms and mucus barriers to thus enhance the synthesis of nitric oxide to kill infections. All formulas were in saline which cannot penetrated biofilms and mucus barriers and were preserved with ineffective low levels of Benzalkonium chloride (BAC) without ethanol that is needed to enhance the efficacy of higher levels of BAC to dissolve biofilms and mucus to allow sodium pyruvate to function properly.

U.S. Pat. No. 11,628,186 B2 Martin, the inventor herein, discloses a synergistic composition to stimulate the synthesis of human lung and sinus surfactants to decrease coughing, increase FEV-1/FVC ratios, decrease lung fibrosis, by increasing apoptosis of myofibroblasts. The therapeutic composition consists of sodium pyruvate in saline and must include compounds that work synergistically to enhance lung surfactants that will enhance lung functions. This patent never taught a method that allows sodium pyruvate to penetrate biofilms and mucus, to thus enhance the synthesis of nitric oxide to kill infections. All formulas were in saline which cannot penetrate biofilms and mucus and were preserved with ineffective low levels of Benzalkonium chloride (BAC) without ethanol that is needed to enhance the efficacy of higher levels BAC to dissolve biofilms and mucus to allow sodium pyruvate to function properly.

United States Patent Application Publication No 11,628, 168 B2 Martin, the inventor herein, discloses a method and composition for the reduction of viral replication, duration and spread of COVID-19 and the flu. The therapeutic composition consists of sodium pyruvate in saline and must include compounds that work synergistically to increase the synthesis of nitric oxide for the reduction of viral replication, duration and spread of COVID-19 and the flu. This patent never taught a method that allows sodium pyruvate to penetrate biofilms and mucus, to thus enhance the synthesis of nitric oxide to kill infections. All formulas were in saline which cannot penetrated biofilms and mucus and were preserved with ineffective low levels of Benzalkonium chloride (BAC) without an alcohol preferably ethanol, that is needed to enhance the efficacy of BAC to dissolve biofilms and mucus to allow sodium pyruvate to function properly.

While all the above patents discuss the use of sodium pyruvate alone or in combination with other ingredients, none of the formulas listed above will work if the patient has a chronic sinus or lung infection that produces a biofilm and mucus and toxins. All the formulas listed above are in saline (water based) with and without calcium, phosphate and magnesium which cannot penetrate biofilm, or mucus barriers or dissolve biofilms to allow pyruvate access to sinus or lung cells to increase its effect as an agent that is an anti-inflammatory, that can increase the synthesis of nitric oxide to kill infections, reduce bacterial toxins and to significantly increase sinus and lung functions, decrease hypoxemia, coughing reflex and reduce inflammatory cytokines that enhance the nerve coughing reflex. None of the patents above teach the use of a formula that will dissolve microbial biofilms and mucus, or a formula which contains sodium pyruvate in saline with 0.06% of Benzalkonium chloride (BAC) and 0.06% ethanal, or isopropanol or methyl alcohol or higher concentrations of each ingredient. Benzalkonium chloride at low levels of 0.02% without an alcohol, preferably ethanol was ineffective at penetrating or eliminating biofilms or mucus and was less effective in killing infections. The equal combination of BAC with Ethanol, isopropanol, or methyl alcohol at least at 0.06% was needed to penetrate biofilms, and mucus allowing sodium pyruvate to reach nasal cells to significantly increase the synthesis of nitric oxide over any other formula to eliminate sinusitis thus eliminate bacteria toxins that damage lung and brain cells. The three components, BAC, with an equal concentration of alcohol, work synergistically with sodium pyruvate to penetrate through biofilms and mucus, thus allow sodium pyruvate to increase the synthesis of nitric oxide, to kill infections, dissolve biofilms and mucus and decrease inflammatory cytokines that cause the coughing reflex of the Vagus nerve.

SUMMARY OF THE INVENTION

The present invention generally relates to compositions and to methods utilizing these unique synergistic compositions that reduce, destroy and penetrate biofilms, mucus barriers and eliminate toxins to deliver drugs that increase the synthesis of nitric oxide that will inhibit the replication, spread, duration and severity of bacterial, virus and fungal ailments, in the lungs or nasal cavity to increase all lung functions and reduce coughing caused by the effect of inflammatory cytokines on nasal nerves. The present invention is also a treatment method to reduce symptoms, including hypoxemia, the cytokine storm and lung fibrosis when biofilms and mucus are destroyed. The present invention is based on the discovery that the pulmonary dysfunction, sinus and lung infections, characteristic of certain disease states, is attributable to the decrease in the synthesis of nasal nitric oxide caused by infections by organisms that produce biofilms and increase mucus and toxins. Inflammatory pathways are upregulated in the nasal epithelium in 40-80% of patients with pulmonary fibrosis, Sinusitis, Idiopathic pulmonary fibrosis, Alzheimer's, Parkinson's, sinusitis and in patients with Cystic fibrosis the majority of which is caused by infections that produce biofilms and mucus barriers and toxins which is part of the etiology of the disease that affects all lung and sinus functions and increases coughing. The production of biofilms and mucus barriers reduces the efficacy of nasal and lung medications that cannot penetrate the biofilm or mucus. This decrease in nasal nitric oxide leads to: decreased sinus and lung functions, increased duration and severity of the sinus and lung infections and production of toxins that damage lung and sinus nerves and brain cells in Parkinsons, and in Alzheimer's and increases inflammatory cytokines, that reduce lung capacity and functions, increases lung fibrosis, coughing, dyspnea, dementia in Alzheimer's, and in Parkinsons. The three components, BAC, with an equal concentration of alcohol, work synergistically with sodium pyruvate to penetrate through biofilms and mucus, thus allow sodium pyruvate to increase the synthesis of nitric oxide, to kill infections, dissolve biofilms and mucus and decrease inflammatory cytokines that cause the coughing reflex of the Vagus nerve.

The present invention composition, which is useful for delivering sodium pyruvate and other drugs through biofilms and mucus barriers to stimulate and increase the synthesis of nasal nitric oxide, that will reduce viral and bacterial replication, duration, spread and counts to reduce the severity of infections, sneezing, reduce coughing, inflammatory cytokines and toxins that effect the Vagus nerve, and to increase lung functions, caused by viruses such as COVID-19 and flu in patients susceptible to these infections, including patients with hypoxemia, asthma, chronic obstructive pulmonary disease, cystic fibrosis, diabetics, long COVID, interstitial lung disease, pulmonary fibrosis, idiopathic pulmonary fibrosis, rhinitis medicamentosa also known as rebound rhinitis, allergic rhinitis, congestion, rebound effects of oxymetazoline, seasonal allergies, sinusitis, with migraines, Alzheimer's, Parkinsons and pulmonary hypertension, includes the following constituents: sodium pyruvate; sodium chloride; benzalkonium chloride; an alcohol selected from: ethanol, isopropanol, methyl alcohol or phenylethyl alcohol; and an aqueous carrier; wherein the composition contains the following amounts of the constituents: sodium pyruvate ranges from about 0.01% to 1%, sodium chloride ranges from 0.45% to 0.93%; benzalkonium chloride ranges from 0.01% to about 0.2% and alcohol ranges from 0.01% to about 0.2%, balance is the aqueous carrier, all percentages by weight.

In some embodiments of the present invention composition, the sodium chloride ranges from 0.6% to 0.93% by weight and is in a saline solution with the aqueous carrier. The preferred composition has benzalkonium chloride ranges from 0.04% to about 0.1% and alcohol ranges from 0.04% to about 0.1%, by weight. Most preferred, benzalkonium chloride content is about 0.06% and the alcohol content is about 0.06%, by weight. The composition alcohol is preferably selected from the group consisting of ethanol, isopropanol and combinations thereof.

The composition aqueous carrier is preferably water selected from the group consisting of purified water and distilled water. A most preferred combination composition contains the following amounts of the constituents: sodium chloride at about 0.9%; sodium pyruvate at about 0.21%, benzalkonium chloride at about 0.06% and alcohol at about 0.06%, all by weight, and especially wherein the composition alcohol is ethanol.

The present invention method for delivering sodium pyruvate and other drugs through biofilms and mucus barriers to stimulate and increase the synthesis of nasal nitric oxide, that will reduce viral and bacterial replication, duration, spread and counts to reduce the severity of infections, sneezing, reduce coughing, inflammatory cytokines and toxins that effect the Vagus nerve, and to increase lung functions, caused by viruses such as COVID-19 and flu in patients susceptible to these infections, including patients with hypoxemia, asthma, chronic obstructive pulmonary disease, cystic fibrosis, diabetics, long COVID, interstitial lung disease, pulmonary fibrosis, idiopathic pulmonary fibrosis, rhinitis medicamentosa also known as rebound rhinitis, allergic rhinitis, congestion, rebound effects of oxymetazoline, seasonal allergies, sinusitis, with migraines, Alzheimer's, Parkinsons and pulmonary hypertension includes: contacting mammalian cells with a therapeutically effective amount of a composition, the composition including the following constituents: sodium pyruvate; sodium chloride; benzalkonium chloride; an alcohol selected from: ethanol, isopropanol, methyl alcohol or phenylethyl alcohol; and, an aqueous carrier; wherein the composition contains the following amounts of the constituents: sodium pyruvate ranges from about 0.01% to 1%, sodium chloride ranges from 0.45% to 0.93%; benzalkonium chloride ranges from 0.01% to about 0.2% and alcohol ranges from 0.01% to about 0.2%, balance is the aqueous carrier, all percentages by weight. Preferred embodiments include all the composition preferences set forth in the immediately above paragraph. In some embodiments, a therapeutic agent is administered relative to contacting the mammalian cells with the composition, and the therapeutic agent is administered at a time selected from the group consisting of: prior to, simultaneously with, and after, contacting the mammalian cells with the composition. In some other embodiments, the method includes a step using an enhancing composition to enhance the efficacy of pulmonary drugs, steroids and cancer medications, where the enhancing composition is administered before and after the treatment.

DETAILED DESCRIPTION OF THE INVENTION

The present invention generally relates to methods utilizing unique synergic compositions that reduce, destroy and penetrate biofilms and mucus barriers to deliver drugs that increase the synthesis of nitric oxide that will inhibit the replication, spread, duration and severity of bacterial, virus and fungal ailments, in the lungs or nasal cavity to increase all lung and sinus functions and reduce coughing caused by the effect of inflammatory cytokines on sinus nerves and protect brain cells from toxins. All the formulas currently used to date are in saline (water based) with and without calcium, phosphate and magnesium which cannot penetrate biofilm, or mucus or dissolve biofilms to allow pyruvate access to sinus or lung cells to increase its effect as an agent that is an anti-inflammatory, that can increase the synthesis of nitric oxide to kill infections, reduce bacterial toxins and to significantly increase lung functions, decrease hypoxemia, coughing and reduce inflammatory cytokines and protect lung and brain cells. The use of a formula that will dissolve microbial biofilms and mucus, to kill infections contains 0.21% or higher sodium pyruvate in saline with 0.06% to 0.1% of Benzalkonium chloride and 0.06% to 0.1% of an alcohol, preferably ethanal or isopropanol, or higher concentrations of each ingredient. Benzalkonium chloride at 0.02% with or without ethanol, or isopropanol was ineffective at penetrating or eliminating biofilms or mucus and was less effective in killing infections. The equal combination of BAC with alcohol at least at 0.06% or higher, was needed to penetrate biofilms, and mucus allowing sodium pyruvate to reach nasal cells to significantly increase the synthesis of nitric oxide which is also needed to devolve biofilms and mucus over any other formula to eliminate sinusitis thus eliminate bacteria toxins that damage sinus, lung and brain cells. Commercial nasal sprays use a variety of alcohols in their nasal sprays, including phenylethyl alcohol, isopropyl alcohol (isopropanol), ethanol, methyl alcohol or higher, all with 0.01% to 0.02% benzalkonium chloride but without sodium pyruvate. Both ethanol and isopropanol can deliver sodium pyruvate through biofilms equally, but isopropanol is generally considered more potent do to its higher molecular weight and has a stronger ability to denature biofilms proteins but is slightly more irritating than ethanol. Thus, in cases when a patient has severe a sinusitis infection, isopropanol is preferred over ethanol to treat that patient. All these formulas have limited use in dissolving biofilms without higher concentrations of benzalkonium chloride, or the presence of sodium pyruvate to increase the synthesis of nitric oxide. Nitric Oxide also acts as a signaling molecule that can trigger biofilm detachment and dispersal in most bacterial species. The three components, BAC, with an equal concentration of alcohol, work synergistically with sodium pyruvate to penetrate through biofilms and mucus, thus allow sodium pyruvate to increase the synthesis of nitric oxide, to kill infections, dissolve biofilms and mucus and decrease inflammatory cytokines that cause the coughing reflex of the Vagus nerve.

Infections that Produce Biofilms

Bacterial biofilms are clusters of bacteria that are attached to a surface and/or to each other and embedded in a self-produced matrix. The biofilm matrix consists of substances like proteins (e.g., fibrin), polysaccharide (e.g., alginate), as well as eDNA. In addition to the protection offered by the matrix, bacteria in biofilms can employ several survival strategies to evade the host defense systems and inhibit antimicrobial drugs and other medications from cells. By staying dormant and hidden from the immune system, they may cause local tissue damage and later cause an acute infection. Within the biofilm, the bacteria adapt to environmental anoxia and nutrient limitation by exhibiting an altered metabolism, gene expression, and protein production, which can lead to a lower metabolic rate and a reduced rate of cell division. In addition, these adaptations make the bacteria more resistant to antimicrobial therapy by inactivating the antimicrobial targets or reducing the requirements for the cellular function that the antimicrobials interfere with. Bacteria are often mutated by pesticides which force the bacteria to produce a more resistant biofilm. During a biofilm infection, simultaneous activation of both innate and acquired host immune responses may occur; neither of which are able to eliminate the biofilm pathogen, but instead accelerate collateral tissue damage. Consequently, biofilm-related diseases are typically persistent infections that develop slowly, are rarely resolved by the immune system, and respond inconsistently to antimicrobial treatments or drugs that treat to congestion. Once established, biofilms may induce changes in the mucociliary blanket like destruction of the epithelial layer and absence of cilia, and a local inflammatory response. This suggests epithelial damage being a part of the pathogenesis of biofilm-associated CRS. CF was the first infection where biofilm was recognized as part of the etiology, and is probably the most thoroughly studied biofilm infection to date. CF is a genetic disease primarily affecting the respiratory and the digestive system, and is characterized by production of viscid mucus and chronic infections. Lung infection is the main cause of morbidity and mortality. In young patients, primarily *S. aureus* and *H. influenzae* colonize in the airways. *P. aeruginosa* dominates at later stages, although other bacterial species also have been seen to form biofilm in the lungs of CF patients. *H. influenzae* in biofilm-like structures have been observed in lung lavage samples from children with CF. Furthermore, clinical isolates formed biofilms on the apical surface of airway epithelium in vitro, and this stimulated epithelium to increased secretion of factors that mediate inflammation. Colonization with *P. aeruginosa* often starts with biofilm in the paranasal sinuses, which serves as reservoirs for repeated lung infections that finally become chronic. *P. aeruginosa* biofilm has been observed in lung tissue, lung abscess, and sputum of CF patients as well as the toxins they produce. Microscopic analyses have shown that *P. aeruginosa* in sputum grows as microcolonies adherent to sputum components. In response to the presence of biofilm, large numbers of polymorphonuclear leukocytes (PMNs) infiltrate the area, producing a chronic inflammation with subsequent tissue damage, loss of lung and sinus function, coughing and obstruction of the airways. The metabolic activity of bacteria and cells consume available oxygen and produce anerobic conditions, which unfortunately seems to favor the biofilm mode of *P. aeruginosa* even more. In patients with IPF (idiopathic pulmonary fibrosis), thirty-eight different bacterial strains were detected in IPF patient sputum. Bacteria-positive results were found in 21.3% to 46% of stable IPF. Fifty-seven different viruses were detected in nasopharyngeal swabs of these IPF patients. Virus-positive nasopharyngeal swabs were found in 18/30 (60%) of tested IPF patients and in 43.3% of stable IPF. IPF patients showed increased inflammatory cytokines (IL-6. IFN-γ, MIG, IL-17, and IL-9) vs. stable IPF and controls. Mortality of IPF patients in one year (39.5%) was higher compared to stable IPF (28.7%).

Sinusitis, Rhinosinusitis (RS) is an inflammation of the nose and the paranasal sinuses, characterized by nasal blockage, obstruction, congestion, production of biofilms and mucus and toxins, or nasal discharge and coughing in many patients with Interstitial lung diseases and in patients with Alzheimer's. Additional symptoms may include loss of smell and facial pain and pressure. According to the duration of the disease, it can be defined as acute when lasting less than 12 weeks, or chronic when lasting more than 12 weeks. Viruses account for up to 80 to 90% of the acute RS, and the most commonly involved viruses are rhinovirus, respiratory syncytial virus, influenza virus, coronavirus, parainfluenza virus, adenovirus, enterovirus and recently COVID-19. The host immune response to a viral infection consists of non-specific and specific components, which will eventually eliminate the invading agent, but also generate dead epithelial and immune cells, creating an environment opportune for secondary bacterial infections. During viral infection in chronic RS, a similar inflammatory process can occur as in acute RS. *S. aureus* biofilm in particular appears to be more pathogenic than other bacterial species, and this has been suggested to be due to a severe local inflammatory response to *S. aureus* superantigens. Colonization in the form of biofilm seems to have a different function in the pathogenesis of *S. pneumoniae* infections. The human nasopharynx is the main reservoir for *S. pneumoniae* and pneumococcal colonization always precedes infection. Striking differences between biofilm residing and dispersed pneumococci indicate that the biofilm phase serves as a non-pathological reservoir. In mouse models, dispersed bacteria displayed inflammatory infiltration, whereas biofilm pneumococci were quickly cleared from the blood without causing invasive disease. Patients with stiff person syndrome have a high level of nasal infections due to viruses and bacteria that produce toxins that enter the blood stream.

Nitric Oxide to Treat Nasal Infections.

Nitric oxide (NO) is also an important signaling molecule between cells which has been shown to have an inhibitory effect on virus infections. We also show here that NO inhibits viral protein and RNA synthesis. Furthermore, we demonstrate that NO generated by inducible nitric oxide synthase, an enzyme that produces NO, inhibits the SARS COV replication cycle. Coronaviruses are enveloped single-stranded positive-sense RNA viruses with genomes of about 27 to 30 kb. Nitric oxide (NO) is an important signaling molecule between cells and is involved in a wide range of processes. An antimicrobial activity of NO has been described for bacteria, protozoa, fungi and for viruses. Nitric Oxide also acts as a signaling molecule that can trigger biofilm detachment and dispersal in most bacterial species. NO is produced by three enzymes that catalyze the oxidation of l-arginine to NO and l-citrulline. Two of the enzymes, neuronal nitric oxide synthase (nNOS) and endothelial NOS (eNOS), are constitutively expressed and are calcium dependent. Inducible NOS (iNOS) is expressed only in activated cells and is calcium independent. The up-regulation of iNOS is common during an infection, and it is known that some viruses and bacteria are inhibited by increased levels of NO. It has also been demonstrated that iNOS is expressed after interferon stimulation in murine macrophages, mouse T cells, human hepatocytes, mononuclear cells, human airway epithelial cells, and alveolar macrophages. Our results demonstrated that NO specifically inhibits the replication cycle of SARS COV, most probably during the early steps of infection, suggesting that the production of NO by iNOS results in an antiviral effect. However, the production of NO should be adjusted to exert antiviral rather than damaging effects. Previous studies have shown that NO plays a role in decreasing the pathogenesis of influenza virus pneumonia in mice and in humans. Sodium pyruvate is an antioxidant that reacts directly with oxygen radicals to neutralize them preventing the formation of Nitrogen dioxide, peroxynitrite to prevents methemoglobin from forming. It can specifically lower the overproduction of superoxide anions. Sodium pyruvate also increases cellular levels of glutathione, a major cellular antioxidant, and increases the synthesis of Nitric Oxide to kill sinus and lung infections.

Influenza virus. There are four types of influenza viruses: A, B, C and D. Human influenza A and B viruses cause seasonal epidemics of disease (known as the flu season) almost every winter in the United States. Influenza A viruses are the only influenza viruses known to cause flu pandemics, i.e., global epidemics of flu disease. A pandemic can occur when a new and very different influenza A virus emerges that both infects people and has the ability to spread efficiently between people. Influenza type C infections generally cause mild illness and are not thought to cause human flu epidemics. Influenza D viruses primarily affect cattle and are not known to infect or cause illness in people. Current subtypes of influenza A viruses that routinely circulate in people include: A (H1N1) and A (H3N2).

Idiopathic pulmonary fibrosis (IPF) and Cystic Fibrosis, belong to a group of conditions called interstitial lung diseases (also known as ILD), which describes lung diseases that involve inflammation or scarring in the lung. There are over 200 other diseases under ILD. Recent data has shown that 80% of these patients have a chronic viral or bacterial infection, with high levels of biofilms and mucus, that inhibit the efficacy of antimicrobials, anti-inflammatory agents, including inhibiting the ability of Sodium pyruvate to decrease coughing, increase lung functions, reduce inflammatory cytokines or increase the synthesis of nitric oxide. IPF is a chronic progressive lung disorder associated with excessive tissue remodeling, scarring, and fibrosis, which makes the lungs unable to effectively transport oxygen into the bloodstream resulting in decreased forced expiratory volume in the first second ($FEV_1$) and forced vital capacity (FVC) values, decreased $SaO_2$, and a decrease in nitric oxide associated with nasal inflammation that causes congestion and coughing. Inflammatory pathways are upregulated in the nasal epithelium in 80% of patients with IPF, and other Idiopathic pulmonary diseases, which is part of the etiology of the disease that affects all lung functions and causes coughing. Nasal inflammation induces oxidative stress, decreases lung functions including $FEV_1$ and FVC values, and increases mucus and coughing. A decrease in total lung functions and capacity results in hypoxemia, dyspnea, and poor quality of life, especially sleep disorders. Blockage of nasal nitric oxide by biofilms or mucus and by inflammation reduces the amount of nitric oxide reaching the lungs, as nitric oxide is a bronchodilator, low levels reduce critical lung functions, leading to increased lung and nasal infections, a reduced $SaO_2$ level, reduced $FEV_1$ and FVC levels also leading to mouth breathing and coughing. Coughing frequency is high in patients with advanced IPF, with median 24-h cough counts of 226 to 520, depending on the population studied. In mild to moderate cases in IPF patients, cough counts vary from 4-57 per 24-h. Strikingly, IPF patients experience more cough symptoms during the daytime (median hourly cough rate 14.6 during the day versus 1.9 during the night). Chronic cough in IPF is not related to age or gender and is more common in advanced disease and in "never-smokers" current treatments for IPF rely mainly on supportive therapies like $O_2$ administration. Nasal steroids and over the counter (OTC) nasal treatments (oxymetazoline) are used, but shut down the synthesis of nasal nitric oxide, which then leads to decreased lung functions and a 34% increase in infections. Nintedanib slows the rate of decline for FVC to 52.3% in 24 weeks compared to the non-treatment group of a 66.7% decline in FVC. Nintedanid has no effect on the treatment of nasal or lung inflammation, infections or biofilms or mucus. Unfortunately, it has numerous side effects, especially on the liver. Pirfenidone has been shown to improve survival as well as improve FVC but also has significant adverse events.

Sodium pyruvate is a natural metabolite that is water soluble and cannot penetrate biofilms or mucus. In patients with bacterial, viral or fungal infections that produce biofilms and mucus, the efficacy of sodium pyruvate was inhibited. Sodium pyruvate in saline in patients without infections, and without biofilms or mucus, is an extracellular antioxidant of the human body, and it has been shown to significantly reduce inflammatory agents throughout the human body, including the lungs and nasal passages, allowing nasal nitric oxide to reach the lungs to increase bronchodilation, thus increase lung functions and decrease coughing. The safety and efficacy of the 0.21% sodium pyruvate nasal spray (N115), in various modified saline delivery formulas, was demonstrated for the treatment of patients with seasonal allergic rhinitis, nonallergic rhinitis, COPD, cystic fibrosis, Long COVID, COVID and pulmonary fibrosis, including IPF. The data was collected from 2,830 over 22 years from the 23 phase 1/2/3 clinical trials. Relevant to this study was the examination of patients with long-COVID, which can cause pulmonary fibrosis. In this open label phase II trial, patient baselines were established for the first 7 days, when there was no treatment, and patient data demonstrated little to no change in symptoms including coughing/sneezing, and trouble breathing. However, after the inhalation of the 0.21% sodium pyruvate nasal spray for the next 7 days, patient data demonstrated clinically and statistically significant improvements in both coughing/sneezing and improved breathing. Similarly, a second open label trial with 15 pulmonary fibrosis patients that remained on their current therapies showed that N115 treatment improved lung function as determined by changes in FVC, $FEV_1$, PEF, and $FEV_1/FVC$ ratios. N115 treatment also reduced coughing in all patients. These results indicated that current therapies in use are inadequate alone to treat patients with IPF with and without infections that produce a biofilm or increase mucus.

Symptoms of Decreased Nitric Oxide, Especially in Patients with Interstitial Lung Diseases.

Decrease in sinus nitric oxide caused by biofilms or mucus, prevents sodium pyruvate that can reduce congestion or inflammation in the nasal cavity and lungs and decrease coughing. Cough is usually the first symptom to develop. It is productive with sputum (phlegm). It tends to come and go at first, and then gradually becomes more persistent (chronic). You may think of your cough as a 'smokers cough' in the early stages of the disease. It is when the breathlessness and hypoxemia begin that people often become concerned.

Breathlessness ('shortness of breath') and wheezing may occur only when you exert yourself at first, for example, when you climb stairs. These symptoms tend to become gradually worse over the years if you continue to smoke. Difficulty with breathing may eventually become quite distressing. The damaged airways generally make a lot more mucus than normal. This forms sputum (phlegm). You tend to cough up a lot of sputum or mucus each day. Chest infections are more common if you have COPD. Wheezing with cough and breathlessness may become worse than usual if you have a chest infection. Sputum usually turns yellow or green during a chest infection.

Hypoxemia is to be understood as and refers to low oxygen in the blood which reduces oxygen to the whole body. Hypoxia is abnormally low oxygen content in any tissue or organ caused by injury, disease or drugs. Patients can have hypoxia, without suffering from Hypoxemia. The two are separate diseases. Chronic hypoxemia symptoms also include lung tightness, breathlessness, coughing, low lung capacity and volume. Hypoxemia can be caused by injury to the lungs, caused by lung and sinus diseases and infections, including COPD, chemicals, ozone, lung cancer, and a host of medications that can injure lung cells and decrease the production of lung surfactants. Patients with hypoxemia are usually on oxygen therapy. Hypoxemia is usually defined in terms of reduced partial pressure of oxygen (mm Hg) in arterial blood, but also in terms of reduced content of oxygen (ml oxygen per dl blood) or percentage saturation of hemoglobin (the oxygen binding protein within red blood cells) with oxygen, which is either found singly or in combination. In an acute context, hypoxemia can cause symptoms such as those in respiratory distress. These include breathlessness, an increased rate of breathing, use of the chest and abdominal muscles to breathe, and lip pursing. However, in a chronic context, and if the lungs are not well ventilated generally, this mechanism can result in pulmonary hypertension, overloading the right ventricle of the heart and causing core pulmonale and right sided heart failure. Polycythemia can also occur. In children, chronic hypoxemia may manifest as delayed growth, neurological development and motor development and decreased sleep quality with frequent sleep arousals. Other symptoms of hypoxemia may include cyanosis, and digital clubbing. Severe hypoxemia can lead to respiratory failure. Many patients with lung or sinus diseases experience Hypoxemia. It can be due to the destruction of the alveoli in the lungs or the inadequate production of lung surfactants that enhance oxygen uptake. Hypoxemia can occur in patients with and without lung or sinus diseases, in patients with lung infections, heavy metal poisoning with metals like cyanide, and the use of inhaled or non-inhaled drugs. It must be noted that there is a difference between people who have transient hypoxemia vs. one that has permanent hypoxemia. Sodium pyruvate in saline given both orally or by inhalation will increase SaO2 levels in people without hypoxemia. Transient hypoxemia (hypoxic endurance) is a self-correcting effect and does not involve lung injury or the inability to synthesize lung surfactants. It occurs in over exercising, mountain climbing etc. Hypoxemia can also be caused by the synthesis of biofilms and mucus that decreases lung gas exchange, increases lung tightness, coughing and decreases lung capacity. Hypoxemia can be caused by malnutrition, by injury to the lungs, caused by lung and sinus diseases like hypertension, COPD and asthma, and infections, diabetes, chemicals, ozone, lung cancer, pulmonary edema, bronchiectasis, bronchiolitis, emphysema, bronchial pneumonia, allergic bronchopneumonia, Allergic Rhinitis, pulmonary fibrosis, Idiopathic pulmonary fibrosis, viral pneumonia, viral and bacterial infections, respiratory mucus, nasal congestion, and encephalitis with retained secretions and a host of medications that can injure lung cells that synthesize lung surfactants. Patients with hypoxemia are usually on oxygen therapy.

Medications Administered by Respiratory Therapy that Cause Hypoxemia and can Inhibit the Synthesis of Nitric Oxide:

The inhaled drugs listed below have some or many of these adverse effects: Hypoxemia, Chest pain, nausea, vomiting, coughing, bronchospasm, headaches, hypoventilation, hypotension, bradycardia, increased infections, blurred vision, mucosal irritation, fatigue, and shortness of breath. Epinephrine, Racemic Epinephrine (Vaponephrinc), Beta-Sympathomimetics: Isoctharinc (Bronkosol), Beta 2 agonist: Metaproterenol (Alupent), Albuterol (Proventil, Ventolin), Terbutalinc, (Brethinc, Bricanyl) Salmeterol (Serevent), Lev-albuterol (Xopenex), Nonsteroidal Anti-Inflammatory Agents: Cromolyn Sodium (Intal), Nedocromil sodium Tilade, Corticosteroids aerosolized Steroids: a. Dexamethasone (Decadron) b. Beclomethasone (Vanceril, beclovent) c. Triamcinolone (Azmacort) d. Flunisolide (Acrobid) and oxymetazoline. Fluticasone propionate (Flovent-a glucocorticoid) f. Budesonide Suspension (Pulmocort), Anticholinergics: Atropine, Ipratropium Bromide (Atrovent) Remdesivir. Steroids like flonase, decrease the synthesis of nasal nitric oxide. Mucolytics/Surface Active Agents Acetylcysteine (Mucomyst). AntiProtozoal Agent. Pentamidine Isethionate (Nebupent) Combination drugs: Combivent (Ipratropium bromide and albuterol sulfate): Advair Diskus (salmeterol and Flovent), Recombinant Human Deoxy ribonuclease I Solution: Dornase Alfa (Pulmozyme, Dupixent, 25 Anti-Viral Agent: Virazole (Ribavirin), Antibiotic: Tobramycin (Tobi) Aminoglycoside antibiotic to treat *Pseudomonas Aeruginosa*, tetracycline, anthracycline antibiotics, Doxorubicin. Oxymetazoline. Cancer drugs that increase hypoxemia include 3-Bromopyruvate, 2-Deoxy-D-glucose, Dichloroacetic acid, Erbitux and Acetylcysteine. Antioxidants have been shown to inhibit damage associated with active oxygen species.

The present invention is directed to a method of elimination of nasal and lung biofilms and mucus to allow sodium pyruvate reach nasal cells and stimulate the synthesis of nasal nitric oxide to inhibit the replication, the severity, duration of and spread of viral, bacterial, fungal infections and toxins. This present invention method is for treating patients that are susceptible to the flu, COVID-19 and other viruses, and bacterial infections, including patients with hypertension, asthma, chronic obstructive pulmonary disease, cystic fibrosis, primary ciliary dyskinesia, diabetes, interstitial lung disease, Idiopathic pulmonary fibrosis, allergic rhinitis, chronic rhinosinusitis, sleep apnea, Alzheimer's, Parkinson's and lung cancer. This method includes contacting mammalian cells with a therapeutically effective amount of a composition that works synergistically that includes the following constituents: sodium pyruvate, ranges from about 0.0001% to about 10%; and sodium chloride ranges from 0.05% to 3.0% and 0.93% being optimum, Benzalkonium chloride from 0.01% to 0.2% with 0.06% being optimum, ethanol ranges from 0.01% to 0.3% with 0.06% being optimum and with a Ph ranging from 5-8, with 7.8 being optimum. The three components, BAC, with an equal concentration of alcohol, work synergistically with sodium pyruvate to penetrate through biofilms and mucus, thus allow sodium pyruvate to increase the synthesis of nitric oxide, to kill infections, dissolve biofilms and mucus and decrease inflammatory cytokines that cause the coughing reflex of the Vagus nerve.

As used herein, the following terms have the given meanings: The term "injured cell" as used herein refers to a cell which has some or all of the following: (a) injured membranes with insufficient synthesis of nitric oxide, lung surfactants that reduce lung gas exchange, that transport through the membranes is diminished and may result in one or more of the following, an increase in toxins and normal cellular wastes inside the cell and/or a decrease in nutrients and other components necessary for cellular repair inside the cell, (b) an increase in concentration of oxygen radicals inside the cell because of the decreased ability of the cell to produce antioxidants and enzymes, and (c) damaged DNA, RNA and ribosomes which must be repaired or replaced before normal cellular functions can be resumed.

The term "pharmaceutically acceptable," such as pharmaceutically acceptable carriers, excipients, etc., refers to pharmacologically acceptable and substantially non-toxic to the subject to which the particular compound is administered. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methane sulfonic acid, oxalic acid, succinic acid, citric acid, malic acid, lactic acid, fumaric acid, and the like. Sample base-addition salts include those derived from calcium, magnesium, ammonium, potassium, sodium, and quaternary ammonium hydroxides, such as for example, tetramethyl-ammonium hydroxide. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems ($6^{th}$ Ed. 1995) at pp. 196 and 1456-1457.

The term "prodrug" or "precursor" refers to compounds that undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "therapeutically effective amount" refers to an amount of a therapeutically effective compound, or a pharmaceutically acceptable salt thereof, which is effective to treat, prevent, alleviate or ameliorate symptoms of a disease. The diseases listed below will cause oxygen saturation levels (SaO2) to fall, which is due to low nitric oxide synthesis and causes Hypoxemia. In smokers 22% suffer from hypoxemia, and in COPD patients 21% have hypoxemia. The pulmonary diseases which cause Hypoxemia and are suitable for treatment by the synergistic formula containing sodium pyruvate with the correct concentrations of benzalkonium chloride, ethanol and correct Ph range are not limited to, acute respiratory distress syndrome (ARDS), acute lung injury, pulmonary fibrosis (idiopathic), Bleomycin induced pulmonary fibrosis, mechanical ventilator induced lung injury, lung transplantation-induced acute graft dysfunction and bronchiolitis obliterans after lung transplantation, bronchial asthma, acute bronchitis, emphysema, chronic obstructive emphysema, chronic obstructive pulmonary disease, centrilobular emphysema, panacinar emphysema, chronic obstructive bronchitis, smoker's disease, reactive airway disease, cystic fibrosis, black lung disease, bronchiectasis, acquired bronchiectasis, kartaagener's syndrome, atelectasis, acute atelectasis, chronic acelectasis, pneumonia, essential thrombocythemia, legionnaire's disease, psittacosis, fibrogenic dust disease, hypersensitivity diseases of the lung, idiopathic infiltrative diseases of the lungs, chronic obstructive pulmonary disorder, adult respiratory distress syndrome, pulmonary tumors, pulmonary hypertension, and diseases caused by organic dust, cyanide poisoning, nicotine, insulin, irritant gases, Alzheimer's, Parkinsons, nasal diseases like allergic rhinitis, sinusitis and chemicals like Cyanide, ozone, lung or sinus infections, inhaled cancer drugs or inhaled drugs, cancer, sleep apnea, and Migraines. Preferred disease states are cystic fibrosis, bronchial asthma, allergic rhinitis, sinusitis, idiopathic pulmonary fibrosis, sinusitis, chronic obstructive pulmonary disease, interstitial lung disease, lung cancer and migraines. Pyruvate Precursors.

In the present invention are the pyruvates and pyruvate precursors with or without the addition of calcium, phosphate and magnesium. Non-limiting illustrative examples of pyruvates include pyruvic acid, sodium pyruvate, potassium pyruvate, magnesium pyruvate, calcium pyruvate, zinc pyruvate, manganese pyruvate, aluminum pyruvate, ammonium pyruvate, lithium pyruvate, and mixtures thereof. Non-limiting illustrative examples of pyruvate precursors include ethyl pyruvate, methyl pyruvate, pyruvyl-glycine, pyruvyl-alanine, pyruvyl-cysteine, pyruvyl-leucine, pyruvyl-valine, pyruvyl-isoleucine, pyruvyl-phenylalanine, pyruvamide, salts of pyruvic acid, and mixtures thereof, with sodium chloride, benzalkonium chloride and ethanol.

Benzalkonium chloride (BAC) is a broad-spectrum antibiotic used as a preservative in most nasal sprays. By itself it has limited ability to penetrate biofilms without an alcohol, (ethanol, isopropanol, methyl alcohol or phenylethyl alcohol). The three components, BAC, at 0.06 to 0.2%, with an equal concentration of alcohol, works synergistically with sodium pyruvate to penetrate through biofilms and mucus, thus allow sodium pyruvate to increase the synthesis of nitric oxide, to kill infections, dissolve biofilms and mucus and decrease inflammatory cytokines that cause the coughing reflex of the Vagus nerve. BAC has a contact time of 3-5 minutes against bacteria, viruses, pathogenic fungi and mycobacteria. 0.02% BAC and 0.02% ethanol is not as effective as the 0.06% or higher BAC and 0.06% to 0.13% ethanol to penetrate through mucus and biofilms. It's the continuous increase in the synthesis of nitric oxide produced by sodium pyruvate over a 24-hour period, that reduces and kills bacteria, viruses, and fungi. Sodium pyruvate also removes the irritation effect of BAC at 0.06% or higher. 72% of patients with Idiopathic pulmonary fibrosis have a continuous nasal infection. BAC has a half-life of 2-3 years in nasal sprays. BAC will breakdown as the Ph decreases below 7.6. Hot weather causes sodium pyruvate to become pyruvic acid, which lowers the Ph. Most commercial nasal saline sprays have concentration of BAC at 0.02% to 0.2% without an alcohol base, to prevent bacterial growth or contamination of the nasal spray from the patient. Thus, if you have sinusitis or a continuous nasal infection a higher level of BAC (0.06% or higher) in combination with 0.06% to 0.13% ethanol or isopropanol and with sodium pyruvate is warranted to prevent contamination of the nasal spray by the patient and to reduce nasal levels of biofilms, mucus and kill infection caused by bacteria, fungi and viruses. At levels above 0.13%, BAC becomes irritating to nasal tissue and nasal cilia. Alcohol, either ethanol, isopropanol, phenyl ethyl alcohol or methyl alcohol are needed to enhance the ability of BAC to penetrate biofilms and kill infections.

The amount of each component present in the therapeutic compositions of the present invention is a therapeutically effective amount. A therapeutically effective amount is the amount to dissolve biofilms and mucus, reduce or eliminate sinus infections, and allow the drug (sodium pyruvate) to reach nasal cells to increase the synthesis of nitric oxide, to treat Hypoxemia, decrease coughing and increase lung functions. The exact amount of each component is a matter of preference subject to such factors as the type of components being employed, the type of condition being treated as well as the other ingredients in the composition. The exact amount of each component will also be determined by whether the pulmonary or nasal cavity is infected or uninfected. This method includes contacting mammalian cells with a therapeutically effective amount of a composition that works synergistically that includes the following constituents: sodium pyruvate, ranges from about 0.0001% to about 10% that increased the synthesis of nasal nitric oxide needed to kill infections and dissolve biofilms and mucus, and sodium chloride ranges from 0.05% to 3.0% and 0.9% being optimum, Benzalkonium chloride (BAC) from 0.01% to 0.3% with 0.06% being optimum, ethanol or isopropanol which ranges from 0.01% to 3% with 0.06% being optimum and a Ph ranging from 7.6-8, with 7.8 being optimum. The three components, BAC, with an equal concentration of alcohol, work synergistically with sodium pyruvate to penetrate through biofilms and mucus, thus allow sodium pyruvate to increase the synthesis of nitric oxide, to kill infections, dissolve biofilms and mucus and decrease inflammatory cytokines that cause the coughing reflex of the Vagus nerve.

In many cases, pulmonary and sinus diseases also have infections that that produce biofilms and mucus that prevent the penetration of sodium pyruvate to reduce inflammation and inflammatory cytokines or to increase the synthesis of nitric oxide to kill the infections and dissolve the biofilm. Such infections may be bacterial, viral, or fungal. The composition may be inhaled first to regulate inflammatory agents followed by nasal inhalation or oral administration of a therapeutic agent. The therapeutic agent may be administered prior to, concomitantly with, or after administration of the inflammatory regulator. The therapeutic agent may be selected from the group consisting of antibacterials, antivirals, antifungals, antitumors, antihistamines, proteins, enzymes, hormones, nonsteroidal anti-inflammatories, cytokines, nicotine, insulin, and steroids.

The antibacterial agents which may be employed in the therapeutic compositions may be selected from a wide variety of water-soluble and water-insoluble drugs, and their acid addition or metallic salts, useful for treating sinus and pulmonary diseases. Both organic and inorganic salts may be used provided the antibacterial agent maintains its medicament value. The antibacterial agents may be selected from a wide range of therapeutic agents and mixtures of therapeutic agents, which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillin's, polypeptides, tetracyclines, cephalosporins, chloramphenicol, and clindamycin. Preferably, the antibacterial agent is selected from the group consisting of bismuth containing compounds, such as, without limitation, bismuth aluminate, bismuth subcitrate, bismuth subgallate, bismuth subsalicylate, and mixtures thereof; the sulfonamides; the nitrofurans, such as nitrofurazone, nitrofurantoin, and furazolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillin's, such as penicillin G, penicillin V, Ampicillin and amoxicillin; the polypeptides, such as bacitracin and polymyxin; the tetracyclines, such as tetracycline, chlortetracycline, oxytetracycline, and doxycycline; the cephalosporins, such as cephalexin and cephalothin; and miscellaneous antibiotics, such as chloramphenicol, and clindamycin. More preferably, the antibacterial agent is selected from the group consisting of bismuth aluminate, bismuth subcitrate, bismuth subgallate, bismuth subsalicylate, sulfonamides, nitrofurazone, nitrofurantoin, furazolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlortetracycline, oxytetracycline, doxycycline, cephalexin, cephalothin, chloramphenicol, clindamycin, Bactorban (Mupirocin), Tobramycin, Pentamidine isethionate, Vancomycin, benzalkonium chloride and silver.

The amount of antibacterial agent which may be employed in the therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the therapeutic composition is present in an amount from about 0.01% to about 10%, preferably from about 0.1% to about 5%, and more preferably from about 1% to about 3%, by weight.

The antiviral agents which may be employed in the therapeutic compositions may be selected from a wide variety of water-soluble and water-insoluble drugs, and their acid addition or metallic salts, useful for treating nasal and pulmonary diseases. Both organic and inorganic salts may be used provided the antiviral agent maintains its medicament value. The antiviral agents may be selected from a wide range of therapeutic agents and mixtures of therapeutic agents, which may be administered in sustained release or prolonged action form. Nonlimiting illustrative categories of such antiviral agents include RNA synthesis inhibitors, protein synthesis inhibitors, immune-stimulating agents, protease inhibitors, and cytokines. Nonlimiting illustrative specific examples of such antiviral agents include the following medicaments. Acyclovir with inhibitory activity against human herpes viruses including herpes simplex types 1 (HSV-1) and 2 (HSV-2), varicella-zoster virus (VZV), Epstein-Barr virus (EBV), and cytomegalovirus (CMV). Foscarnet sodium is an organic analogue of inorganic pyrophosphate that inhibits replication of all known herpes viruses in vitro including cytomegalovirus (CMV), herpes simplex virus types 1 and 2 (HSV-1, HSV-2), human herpes virus 6 (HHV-6), Epstein-Barr virus (EBV), varicella zoster virus (VZV), and Remdesivir.

Ribavirin has antiviral inhibitory activity in vitro against respiratory syncytial virus, influenza virus, and herpes simplex virus. Vidarabine possesses in vitro and in vivo antiviral activity against Herpes simplex virus types 1 and 2 (HSV-1 and HSV-2), and in vitro activity against varicella-zoster virus (VZV). Ganciclovir inhibits replication of herpes viruses both in vitro and in vivo. Sensitive human viruses include cytomegalovirus (CMV), herpes simplex virus-1 and -2 (HSV-1, HSV-2), Epstein-Barr virus (EBV), and varicella zoster virus (VZV). Zidovudine is an inhibitor of the in vitro replication of some retroviruses including HIV (also known as HTLV III, LAV, or ARV). Phenol (carbolic acid) is a topical antiviral, anesthetic, antiseptic, and anti-pruritic drug. Amantadine hydrochloride (1-adamantan-amine hydrochloride, SYMMETREL®) has pharmacologi-cal actions as both an anti-Parkinson and an antiviral drug against influenza A. Interferon □-n3 (human leukocyte derived, ALFERON®) proteins for use by injection. Inter-ferons are naturally occurring proteins with both antiviral and antiproliferative properties. Interferon □-2a (recombi-nant, ROFERON-A®). The mechanism by which Interferon □-2a, recombinant, exerts antitumor or antiviral activity is not clearly understood. 20 Oseltamivir ((3R,4R,5S)-4-acety-lamino-5-amino-3-(1-ethylpropoxy)-1-cyclohexenel-car-boxylic acid ethyl ester, TAMIFLU®) is a is an antiviral drug that is used in the treatment and prophylaxis of both influenza virus A and Influenza virus B. Zanamivir. Paxlovid. Preferred antiviral agents to be employed may be selected from the group consisting of acyclovir, foscarnet sodium, Ribavirin, vidarabine, Ganciclovir sodium, zidovu-dine, phenol, amantadine hydrochloride, and interferon alpha-n3, interferon-2a, and Oseltamivir. In a preferred embodiment, the antiviral agent is selected from the group consisting of acyclovir, foscarnet sodium, Zanamivir, Riba-virin, vidarabine, valacydvir, famiclour, Tenofovir, Viread, Paxlovid, silver and Ganciclovir sodium. In a more preferred embodiment, the antiviral agent is Remdesivir.

The amount of antiviral agent which may be employed in the therapeutic compositions of the present invention may vary depending upon the therapeutic dosage recommended or permitted for the particular antiviral agent. In general, the amount of antiviral agent present is the ordinary dosage required to obtain the desired result. Such dosages are known to the skilled practitioner in the medical arts and are not a part of the present invention. In a preferred embodi-ment, the antiviral agent in the therapeutic composition is present in an amount from about 0.1% to about 20%, preferably from about 1% to about 10%, and more prefer-ably from about 2% to about 7%, by weight.

The antifungal agents which may be employed in the therapeutic compositions may be selected from a wide variety of water-soluble and water-insoluble drugs, and their acid addition or metallic salts, useful for treating pulmonary diseases. Both organic and inorganic salts may be used provided the antifungal agent maintains its medicament value. The antifungal agents may be selected from a wide range of therapeutic agents and mixtures of therapeutic agents, which may be administered in 15 sustained release or prolonged action form. Nonlimiting illustrative specific examples of antifungal agents include the following medi-caments: miconazole, clotrimazole, tioconazole, tercona-zole, povidone-iodine, silver and butoconazole. Other anti-fungal agents are lactic acid and sorbic acid. Preferred antifungal agents are miconazole and clotrimazole. The amount of antifungal agent, which may be employed in the therapeutic compositions of the present invention may vary depending upon the therapeutic dosage recommended or permitted for the particular antifungal agent. In general, the amount of antifungal agent present is the ordinary dosage required to obtain the desired result. Such dosages are known to the skilled practitioner in the medical arts and are not a part of the present invention. In a preferred embodi-ment, the antifungal agent in the therapeutic composition is present in an amount from about 0.05% to about 10%, preferably from about 0.1% to about 5%, and more prefer-ably from about 0.2% to about 4%, by weight.

The antitumor agents which may be employed in the therapeutic compositions may be selected from a wide variety of water-soluble and water-insoluble drugs, and their acid addition or metallic salts, useful for treating pulmonary diseases. Both organic and inorganic salts may be used provided the antitumor agent maintains its medicament value. The antitumor agents may be selected from a wide range of therapeutic agents and mixtures of therapeutic agents, which may be administered in sustained release or prolonged action form. Nonlimiting illustrative specific examples include anti-metabolites, antibiotics, plant prod-ucts, hormones, and other miscellaneous chemotherapeutic agents. Chemically reactive drugs having nonspecific action include alkylating agents and N-alkyl-N-nitroso com-pounds. Examples of alkylating agents include nitrogen mustards, aziridines (ethylenimines), sulfonic acid esters, and epoxides. Anti-metabolites are compounds that interfere with the formation or utilization of a normal cellular metabolite and include amino acid antagonists, vitamin and coenzyme antagonists, and antagonists of metabolites involved in nucleic acid synthesis such as glutamine antago-nists, folic acid antagonists, pyrimidine antagonists, and purine antagonists. Antibiotics are compounds produced by microorganisms that have the ability to inhibit the growth of other organisms and include actinomycin's and related anti-biotics, glutarimide antibiotics, sarkomycin, fumagillin, streptonigrin, tenuazonic acid, actinogan, peptinogan, and anthracyclic antibiotics such as doxorubicin. Plant products include colchicine, podophyllotoxin, and vinca alkaloids. Hormones include those steroids used in breast and prostate cancer and corticosteroids used in leukemia and lymphomas. Other miscellaneous chemotherapeutic agents include ure-thane, hydroxyurea, and related compounds; thiosemicarba-zones and related compounds; phthalimide and related com-pounds; and triazene's and hydrazine's, 3Bromopyruvate, 2-Deoxy-D glucose, Dichloroacetic acid. The anticancer agent may also be a monoclonal antibody or the use of X-rays. In a preferred embodiment, the anticancer agent is an antibiotic. In a more preferred embodiment, the antican-cer agent is doxorubicin. In a most preferred embodiment, the anticancer agent is doxorubicin.

Lung Cancer-Medications Chemotherapy is called a sys-temic treatment because the medicines enter your blood-stream, travel through your body, and kill cancer cells both inside and outside the lung area. Some chemotherapy drugs are taken by mouth (orally), while others are injected into a vein (intravenous, or IV). Some of the more common chemotherapy medicines used for lung cancer includes the following: Bevacizumab, Carboplatin, Cisplatin, Crizotinib, Docetaxel, Erlotinib, Etoposide, Gemcitabine, Irinotecan, Paclitaxel, Pemetrexed Vinorelbine.

Antifibrotic drugs for Interstitial lung disease including Idiopathic pulmonary fibrosis include Ofev, Nintedanid and Esbrient.

Most chemotherapy or antifibrotic drugs causes some side effects, including destruction of mitochondria which causes an insufficient synthesis of lung surfactants that lead to hypoxemia and reduces the ability of cancer cells to undergo Apoptosis, coughing, difficulty breathing and allergic reac-tions.

The amount of antitumor agent or antifibrotic drugs, which may be employed in the therapeutic compositions of the present invention may vary depending upon the thera-peutic dosage recommended or permitted for the particular antitumor agent. In general, the amount of antitumor agent present is the ordinary dosage required to obtain the desired result. Such dosages are known to the skilled practitioner in the medical arts and are not a part of the present invention. In a preferred embodiment, the antitumor agent or antifibrotic in the therapeutic composition is present in an amount from about 1% to about 50%, preferably from about 10% to about 30%, and more preferably from about 20% to about 25%, by weight. The carrier composition is selected from the group consisting of tablets, capsules, liquids, isotonic liquids, isotonic media, enteric tablets and capsules, parenteral, topicals, creams, gels, ointments, chewing gums, confections and the like. The favored method of delivery is through inhalation by mouth or sinuses. Also, the elimination of anaphylaxis caused by any things including cancer drugs and the treatment of anaphylaxis with epinephrine.

Obviously, numerous modifications and variations of the present invention are possible in the light of the above teachings, and the invention is not limited to the examples herein. It is therefore understood that within the scope of the appended claims, the invention may be practiced otherwise than as specifically described herein. Throughout this application, various publications have been referenced. The disclosures in these publications are incorporated herein by reference in order to more fully describe the state of the art.

The compounds of the present invention can be prepared according to the examples set out below. The examples are presented for purposes of demonstrating, but not limiting, the preparation of the compounds and compositions of this invention.

Although particular embodiments of the invention have been described in detail herein with reference to the accompanying drawings, it is to be understood that the invention is not limited to those particular embodiments, and that various changes and modifications may be affected therein by one skilled in the art without departing from the scope or spirit of the invention as defined in the appended claims.

Example 1 Study Design Overview

The studies listed below enrolled patients with confirmed chronic sinusitis with various sinus and lung diseases and with patients with various sinus and lung diseases without sinusitis (table 1), into this clinical study. The patients without nasal infections or sinusitis that produces biofilms included patients with COPD, Allergic Rhinitis, Seasonal allergies, congestion, pulmonary fibrosis with COPD, Long COVID, COVID-19, the flu, Idiopathic pulmonary fibrosis, and the common cold all without a secondary infection. The other patients with a nasal infection and sinusitis that produced biofilms, included patients with COVID-19, Long COVID, Chronic obstructive pulmonary disease (COPD), pulmonary fibrosis, Idiopathic pulmonary fibrosis (IPF), Cystic fibrosis (CF), Interstitial lung diseases, Allergic Rhinitis, the flu, Alzheimer's, Parkinsons, and patients with pulmonary hypertension. Every attempt was made to include women and minorities. The patients were their own controls. Data from each patient was collected for FEV-1, FVC, nitric oxide, nasal inflammation, congestion, coughing, infections levels, and Sa02, prior to receiving any treatment with sodium pyruvate, and then measured over a 21 day period with the sodium pyruvate treatment formulas. No patients withdrew from the study. No adverse events were reported. Benzalkonium chloride (BAC) is used in various formulas from 0.02% to 0.2%, but because BAC over 0.13% is irritating to the sinus cavity a 0.06% was used and as effective as the higher doses. Equal parts of ethanol enhance the effect of BAC to penetrate and dissolve biofilms and mucus as tested in laboratory tests as did isopropanol or methyl alcohol. Ethanol was chosen because it is less irritating to nasal mucosa. Other preservatives and actives for nasal sprays that have been tested with the 0.21% sodium pyruvate include benzoic acid, methyl parabens, benzyl alcohol, potassium benzoate, phenylethyl alcohol, alcohol, disodium phosphate, phenylcarbinol, monosodium phosphate, polyhexamethylene biguanide, phenol, thimerosal sodium borate, potassium dichromate, camphor, menthol, oxymetazoline, eucalyptol, pyrrolidine carboxylic acid, and cromolyn sodium. N-acetylcysteine was also used in an attempt to dissolve mucus, thus allowing sodium pyruvate (N115) to reach nasal cells. BAC at 0.06% or higher with 0.06% ethanol or higher or isopropanol were more effective than the other preservatives or actives tested. The other preservatives or active ingredients for nasal sprays, including oxymetazoline, with 0.21% sodium pyruvate were all moderately effective when compared to BAC and ethanol, (increasing nitric oxide from 5%-25% but not to 38% or more). All of them can cause nasal irritation without the addition of sodium pyruvate, especially oxymetazoline which produces a rebound effect. In clinical trials, the rebound effect of oxymetazoline was eliminated when 0.21% sodium pyruvate was added to the formula. After testing all of the preservatives, only BAC and ethanol or isopropanol worked synergistically with sodium pyruvate to penetrate and destroy biofilms and mucus and did not react with sodium pyruvate, as demonstrated in 4 years of stability testing. The types of bacteria, besides viruses, which commonly cause bacterial sinusitis include: *Streptococcus pneumoniae, Hemophilus influenzae, Staphylococcus aureus, Moraxella catarrhalis*, and *pseudomonas acruginosa*. As detailed above, bacterial sinusitis often follows a cold or flu infection. The use of pesticides has been found to mutate organisms like *pseudomonas* which then produces a more resistant biofilm that infects the nasal cavity and gut microbiota, which also produces toxins that infect other parts of the body making it difficult to treat. All patients with a diagnosis of Sinusitis had their nasal cavity swabbed and the bacterial or viral infections were identified and counted. The nasal cavity swabs and lavage were taken prior to receiving the sodium pyruvate formulas as a baseline measurements. Mucus and biofilms were still present at 21 days for the placebo groups. Treating patients with 0.21% sodium pyruvate in the 0.06% BAC and 0.06% ethanol or isopropanol with 0.9% saline nasal spray increased the synthesis of nasal nitric oxide that reduced bacterial or viral counts over the 21 days by 5-6 logs or more (from a count of over 1,000,000 to less than 10). Also, mucus and biofilms disappeared from the nasal swab lavage testing in the sodium pyruvate treated patients. Coughing was also dramatically reduced in all sodium pyruvate treated patients. All preservatives by themselves do not increase the synthesis of nasal nitric oxide, FEV-1 or $SaO_2$, except when sodium pyruvate is included in the formulation. All preservatives only have an effective treatment time of 3-8 minutes, whereas sodium pyruvate increases the synthesis of nasal nitric oxide that lasts weeks even after no treatment is used. All formulas were at a Ph 0f 7.4-7.8 buffered with potassium phosphate.

Table 1. Testing a nasal spray with 0.21% sodium pyruvate, 0.9% saline formula with 0.02% Benzalkonium chloride and 0.02% ethanol against nontreatment at day zero, in patients with a lung or sinus disease, and with congestion and nasal inflammation due to seasonal allergies, but without moderate or severe sinus infections or sinusitis or biofilms produced from secondary infections like *pseudomonas*. Some of these patients may have had very mild sinusitis. In previous testing of various concentrations of sodium pyruvate, the 0.21% produced the best results carried in 0.90% sodium chloride with 0.02% benzalkonium chloride with or without 0.02% ethanol. Overall rating was 1-10 with 1 being the most negative and 10 being the best result for reduction of congestion and nasal inflammation. This is the formula with or without ethanol was used in 8 human clinicals with approximately these same results in patients with no moderate or severe sinusitis or sinus infections that produce biofilms and copious amounts of mucus. The patient's data was composited to obtain the data below. The patients treated included patients with COPD, Allergic Rhinitis, Seasonal allergies, congestion, pulmonary fibrosis with COPD, Idiopathic pulmonary fibrosis, Long COVID, COVID-19, the flu, and the common cold all without a secondary infection or biofilms or copious amounts of mucus. Patients were evaluated over 21 days with the sodium pyruvate formula against their own base line measurements taken prior to treatment with the sodium pyruvate formulas. The testing results without ethanol were identical to the formula with ethanol listed below. BAC and Ethanol at higher concentrations are needed when biofilms are present.

TABLE 1

| 0.21% Na pyruvate in saline with 0.02% BAC and 0.02% ethanol | Percentage Increase in FEV-1 over (baseline) at 21 days | Percentage increase of Nitric Oxide over 21 day baseline | Nasal inflammation 1-10 | Relief of coughing percentage decrease over 21 day baseline | Percentage Increase in SaO2 over baseline decrease in hypoxemia | Overall decrease of infection numbers in logs |
|---|---|---|---|---|---|---|
| No biofilms No sinusitis | 21.0 | 38.0% | 9.8 | 59 | 5 | 0.5 |

Table II. Comparison of a nasal spray with 0.21% sodium pyruvate 0.9% saline formula with 0.02% Benzalkonium chloride with the addition of 0.02% ethanol in patients with a lung disease and sinus infections, sinusitis, including viral infections and *pseudomonas*, against (baseline) measurements. 70% of patients with idiopathic pulmonary fibrosis (IPF) and patients with pulmonary fibrosis and COPD have nasal infections, with biofilms, and moderate to severe mucus. Overall rating was 1-10 with 1 being the most negative and 10 being the best result for reduction of inflammation. The biofilm and infections blocked the efficacy of the sodium pyruvate formula to penetrate biofilms and increase the synthesis of nitric oxide. At the end of 21 days of treatment with the pyruvate formula, in 86 patients, 25% still tested positive for sinusitis and infections. It was obvious from the data obtained that the 0.02% benzalkonium even with 0.02% ethanol were not the correct concentrations to treat patients with nasal infections that produce biofilms and mucus.

TABLE II

| pyruvate in saline with 0.02% BAC and 0.02% ethanol | Percentage Increase in FEV-1 over baseline at 21 days | Percentage increase of Nitric Oxide over baseline at 21 days | Nasal inflammation 1-10 | Relief of coughing percentage decrease at 21 days from baseline | Percentage Increase in SaO2 over baseline decrease in hypoxemia | Overall decrease of infection numbers in logs |
|---|---|---|---|---|---|---|
| with nasal infections and biofilm & mucus | 12.4 | 19.0% | 9.5 | 26 | 2 | 1.1 |

Table III. Comparison of a nasal spray with 0.21% sodium pyruvate 0.9% saline formula with 0.06% Benzalkonium chloride (BAC) and 0.06% ethanol or isopropanol, for 21 days in patients with a lung disease and sinus infections, including a viral infections sinusitis, *pseudomonas* especially in CF patients and lots of mucus. Overall rating was 1-10 with 1 being the most negative and 10 being the best result for reduction of inflammation. Please note that higher concentrations of BAC and ethanol or isopropanol were just as effective at the 0.06% level for both. 0.1% for BAC and ethanol or isopropanol was effective as was 0.2% of BAC and Ethanol or isopropanol. The least irritating formula was the 0.06% of the BAC and 0.06% ethanol or isopropanol. The increased synthesis of Nitric oxide increases its mucolytic and bronchial dilator effect. It is an effective short-acting bronchodilator. This effect contributes to the removal of secretions and maintains airway functions. Nitric oxide has also been seen to control ciliary beat frequency in the airways. The increased synthesis of nitric oxide eliminated the bacterial, viral or fungal infections including *pseudomonas* in 15 CF patients and eliminated the patient's sinusitis. 16 Patients tested included patients with Idiopathic pulmonary fibrosis p=0.0001 and 56 patients with other lung diseases including 12 patients with COPD and sinusitis p=0.001. The same percentages, within 4%, were achieved when ethanol was substituted for isopropanol or methyl alcohol. Isopropanol did relieve coughing by 80%, nitric oxide increases 45% but had a nasal inflammation of 7. Benzalkonium chloride at 0.06% to 0.1% with 0.03% isopropanol, was as effective as 0.06% ethanol, because Isopropanol has a better ability to penetrate biofilms and dissolve biofilms. Ethanol is less irritating than isopropanol.

TABLE III

| pyruvate in saline with 0.06% BAC & 0.06% ethanol | Percentage Increase in FEV-1 over 21 day (baseline) | Percentage increase of Nitric Oxide over 21 day baseline | Nasal inflammation 1-10 | Relief of coughing percentage decrease in 21 days | Percentage Increase in SaO2 over baseline, decrease in hypoxemia | Overall decrease of infection numbers in logs |
|---|---|---|---|---|---|---|
| nasal infections & biofilms | 26.0 | 39.0% | 8.9 | 73 | 8 | 5.1 |

Table IV. Comparison of a nasal spray 20 mM (0.21%) sodium pyruvate 0.9% saline formula with 0.06% Benzalkonium chloride and 0.0% ethanol or isopropanol in 67 patients with a lung disease and sinus infections, including a viral infection and predominately *pseudomonas* and biofilms and mucus. Overall rating was 1-10 with 1 being the most negative and 10 being the best result for reduction of mucus. The elimination of ethanol or isopropanol reduced the efficacy of BAC and sodium pyruvate. Sinusitis was not completely eliminated.

TABLE IV

| pyruvate in saline with 0.06% BAC no ethanol | Percentage Increase in FEV-1 over 21 day baseline | Percentage increase of Nitric Oxide over 21 day baseline | Nasal inflammation 1-10 | Relief of coughing percentage decrease in 21 days from baseline | Percentage Increase in SaO2 over baseline decrease in hypoxemia | Overall decrease of infection numbers in logs |
|---|---|---|---|---|---|---|
| with nasal infections & biofilms | 15.0 | 20.0% | 9.1 | 49 | 3 | 3.6 |

Table V. Comparison of a saline nasal spray of (0.0%) sodium pyruvate 0.9% saline formula with 0.06% Benzalkonium chloride and 0.06% ethanol or isopropanol (placebo) in patients with a lung disease and with sinus infections, sinusitis, predominately *pseudomonas*. Overall rating was 1-10 with 1 being the most negative and 10 being the best result for reduction of mucus. The 34 patients with sinusitis increased from mild to moderate.

TABLE V

| No pyruvate in saline with 0.06% BAC & 0.06% ethanol placebo | Percentage Increase in FEV-1 over 21 day baseline | Percentage increase of Nitric Oxide over 21 day baseline | Nasal inflammation 1-10 | Relief of coughing percentage decrease over 21 day baseline | Percentage Increase in SaO2 over baseline decrease in hypoxemia | Overall decrease of infection numbers in logs |
|---|---|---|---|---|---|---|
| with nasal infections & biofilms | 0 | −28% | 3.2 | 3 | −4 | 1.0 |

Table VI. Comparison of a nasal spray of (0.21%) sodium pyruvate 0.9% saline formula with 0.00% Benzalkonium chloride and 0.06% ethanol or isopropanol in patients with a lung disease and with sinus infections, sinusitis, predominately *pseudomonas* biofilms and mucus. Overall rating was 1-10 with 1 being the most negative and 10 being the best result reduction of mucus. The 42 patients' level of sinusitis increased from mild to moderate.

24

TABLE VI

| pyruvate in saline with no BAC & 0.06% ethanol | Percentage Increase in FEV-1 over 21 day baseline | Percentage increase of Nitric Oxide over 21 day baseline | Nasal inflammation 10 | Relief of coughing percentage decrease in 21 days over baseline | Percentage Increase in SaO2 over baseline decrease in hypoxemia | Overall decrease of infection numbers in logs |
|---|---|---|---|---|---|---|
| with nasal infections & biofilms | 4 | 8% | 7.5 | 18 | 2 | 1.6 |

Table VII. Comparison of various nasal sprays with (0.21%) sodium pyruvate (N115) 0.9% saline formula with various percentages of Benzalkonium chloride and an equal percentage of alcohol in patients with a lung disease and with moderate to severe sinus infections, sinusitis with biofilms against baseline measurements over a 21-day period. These patients had viral infections and half had secondary bacterial infections. Overall log reduction of infections over the 21 days is listed below. Overall rating for inflammation was 1-10 with 1 being the most negative and 10 being the best result for nasal inflammation. Overall the 0.06% BAC and 0.06% ethanol or isopropanol was the best, whereas the 0.1% had a sting to it and the 0.2 was irritating but effective at 21 days. Sodium pyruvate decreases the nasal irritation caused by BAC. The only formulas to eliminate biofilms, mucus and nasal infection and sinusitis were the formulas with nitric oxide levels over 21%. Also, sodium pyruvate reduced the cytokines that stimulate the coughing nerve to become overactive, specifically the cytokine storm. To measure inflammatory cytokines nasal lavage samples were measured by multiplex bead-based assay and by enzyme linked immunosorbent assay (Elisa) in 20 patients. When measured, N115 lowered TNF-alpha by 90%, interleukin-1 beta by 87%, interleukin-8 by 93%, interleukin 10 and 6 by 74% and interferon-gamma by 69% at the end of the 21 day testing period, which are primarily associated with causing coughing by triggering inflammation in the airway, which can sensitize nerve ending and lead to a cough reflex. N115 eliminated the inflammatory response that stimulate cough receptors to sensitizes the nerve ending that leads to a cough reflex. The testing of isopropanol, methyl alcohol, and Phenyl Ethyl Alcohol in the nasal spray at concentrations of 0.02% to 0.5%, with 0.06% BAC and 0.21% sodium pyruvate produced the same results as listed in table VII with 0.06% to 0.1% being the optimum concentration for each of the alcohols and nearly identical to the 0.06% ethanol results listed below. Ethanol was used because it is the least irritating alcohol of the alcohols.

TABLE VII

| 0.21%pyruvate in saline with various percentages of BAC and ethanol | Percentage Increase in FEV-1 over (baseline) at 21 days | Percentage increase of Nitric Oxide over baseline at 21 days | Nasal inflammation 1-10 | Relief of coughing percentage decrease at 21 days over baseline | Percentage Increase in SaO2 over baseline at 21 days | Overall decrease of infection numbers in logs |
|---|---|---|---|---|---|---|
| 0.02% BAC & 0.02% ethanol | 12.4 | 19.0 | 9.5 | 26 | 2 | 1.1 |
| 0.06% BAC & 0.06% ethanol | 26.0 | 38.0 | 8.9 | 73 | 8.0 | 5.1 |
| 0.1% BAC & 0.1% ethanol | 24.0 | 39.6 | 7.9 | 86 | 5.0 | 5.0 |
| 0.2% BAC & 0.2% ethanol | 19.0 | 28.0 | 3.7 | 93 | 3.0 | 6.1 |
| No pyruvate 0.06% BAC & 0.06% ethanol | 0 | -28 | 3.2 | 3 | -4 | 1.0 |
| Placebo 0.21% sodium pyruvate 0.06% BAC no ethanol | 15 | 20 | 9.1 | 49 | 3 | 3.6 |
| 0.21% sodium pyruvate with no BAC and 0.06% ethanol | 4 | 8 | 7.5 | 18 | 2 | 1.6 |
| 0.21% sodium pyruvate no BAC, no ethanol | 5 | 4 | 6.2 | 10 | 1 | 0.5 |

Conclusions from Tables 1-7. As demonstrated in the above tables I-VII, the use of benzalkonium chloride (BAC) and ethanol without sodium pyruvate (placebo) will not decrease biofilms and mucus or decrease coughing. This formula (placebo) also increases nasal irritation, cannot treat hypoxemia, and suppresses the synthesis of nitric oxide, needed to statistically increase lung functions and kill infections. All the formulas including the formula that contained the 0.21% sodium pyruvate in 0.9% saline, and 0.06% BAC with 0.06% ethanol or Isopropanol or methyl alcohol, were tested against baseline measurements at day 0 then the results compared to the 21-day results. The 0.21% sodium pyruvate in 0.9% saline, and 0.06% BAC with 0.06% ethanol demonstrated an increase of 26% FEV-1 values (p=0.004), increased the production nitric oxide over 38% (p=0.003), SaO2 values, produced clinically and statistically significant results, as well as a significant reduction of nasal inflammation caused by inflammatory cytokines and a decrease of coughing by 73%. Increasing BAC to higher levels (0.1-0.2%), produces more nasal irritation. By removing BAC or ethanol, the efficacy dropped dramatically, BAC functions better with the presence of ethanol. Most sinus nasal sprays use BAC without ethanol, Isopropanol or methyl alcohol which explains the lack of efficacy. An alcohol is needed to enhance the efficacy of BAC to dissolve biofilms and sodium pyruvate to reach nasal cells to produce nitric oxide. Other preservatives like benzoic acid, methyl parabens, benzyl alcohol, K benzoate, phenylethyl alcohol, phenol, N-acetylcysteine, polyhexamethylene biguanide and thimerosal used by themselves, without sodium pyruvate decrease nitric oxide by -10 to -28%, did not increase FEV-1 and reduced SaO2 levels-4 t0-6%. The addition of 0.21% sodium pyruvate slightly increased nitric oxide by 5-21%, FEV-1 by 6-12% and SaO2 levels by 1-3% with these other preservatives. In the testing below Isopropanol was equally effective as ethanol with BAC to destroy biofilms and reduce bacterial logs.

In laboratory tests. *Pseudomonas* was grown to produce biofilms. To this *pseudomonas* broth, mucus was added to simulate sinusitis in the nasal cavity. The biofilm and mucus were concentrated and to that 100 ml of test formula was added. It was then tested with various formulas to determine if the formula could dissolve and eliminate the biofilm and mucus and *pseudomonas*. It can take several hours to dissolve. Ethanol (A) at 0.06% did not completely dissolve the biofilm and mucus, especially at lower concentrations. At the end of 7 hours, only 10% of the biofilm and mucus dissolved. Isopropanol dissolved biofilms by 27%. BAC (B) at 0.06% can be effective at destroying biofilms and mucus. It can reduce the thickness of the biofilm and mucus. At the end of seven hours, 28% of the biofilm and mucus was dissolved. Nitric oxide (C) can effectively dissolve biofilms and mucus. It was added at concentrations equal to those found in the nasal cavity to simulate the effect you get from the synthesis of nitric oxide produced from sodium pyruvate. It destroys biofilm's structure. At the end of seven hours, 46% of the biofilm and mucus was dissolved. Various combinations like BAC and ethanol or isopropanol (D) worked synergistically to reduce the biofilm and mucus by 39%. BAC and nitric oxide [E] dissolve biofilm and mucus by 64% at the end of seven hours. The combination of ethanol and nitric oxide (F) dissolved the biofilm and mucus by 42%. When nitric oxide was added to simulate its synthesis by sodium pyruvate, to 0.06% BAC and 0.06% ethanol, (G) 91% of the biofilm and mucus were dissolved. The combination of isopropanol, BAC and nitric oxide dissolved the biofilm by 97% and reduced log counts by 6.7 logs. The reason that ethanol was used is because it was slightly less irritating to patients. Only the triple combination reduced log counts of *pseudomonas* by 6.1. All the other formulas reduced log counts of *pseudomonas* by 1-2 logs. A B C D E F G Eth BAC NO BAC/Eth BAC/NO Eth/NO Eth/BAC/NO 10% 28% 46% 39% 64% 42% 91% Log reduction of *pseudomonas* at seven hours of treatment from the untreated counts of 6.1 logs. 0.5 2.1 1.7 2.2 2.3 2.1 6.1

Table 8. A comparison of the efficacy of various sodium pyruvate formulas in different delivery formulas for Oral, and nasal delivery. As an example, the oral formulas cannot treat nasal infections or sinusitis and without BAC and ethanol or isopropanol, cannot penetrate biofilms, mucus or kill infections. Combinations of oral and nasal formulas work synergistically. The oral lung surfactant formula which increases lung function and treats lung fibrosis, contains 0.05% to 0.21% sodium pyruvate, 0.61 to 0.9% sodium chloride with 0.01 to 0.15% calcium chloride, 0.011 to 0.11% magnesium chloride and 0.03% potassium phosphate with no BAC or ethanol. In table 8 the 0.01% of calcium chloride, 0.01% magnesium chloride and 0.03% of potassium phosphate were added to 0.9% saline with the 0.21% pyruvate to give you a 1.16% total salt solution which is isotonic. If you use the 0.15% calcium chloride, with 0.11% magnesium chloride with 0.30% potassium phosphate, with 0.21% sodium pyruvate the saline must be reduced to 0.45% to be in the isotonic range. The amount of each ingredient is dependent on the severity of the lung or sinus disease. It was surprising and unexpected to see that the addition of CaCl, MgCl, and k phosphate would enhance the efficacy of the 0.21% sodium pyruvate with 0.06% BAC and 0.06% ethanol.

TABLE VIII

| Table 8 Formulas with different capabilities. | 0.90% NaCl, 0.21% Na pyruvate, no preservatives, no BAC, no ethanol No Sinusitis only COPD and Allergic Rhinitis (AR) 78 patients oral delivery | 0.90% NaCl, 0.21% Na pyruvate, 0.02% BAC, 0.02% ethanol. No Sinusitis but mucus Nasal delivery for AR 46 patients | 0.90% NaCl, 0.21% Na pyruvate, 0.02% BAC and 0.02% ethanol or Isopropanol Sinusitis with mucus and biofilms Nasal delivery 36 patients | 0.9% NaCl, 0.21% Na pyruvate, 0.06% BAC and 0.06% ethanol. Sinusitis with mucus and biofilms Nasal delivery 27 patients | 0.9% NaCl CaCl, MgCl and potassium phosphate, 0.21% Na pyruvate 0.06% BAC and 0.06% Ethanol Sinusitis with mucus and biofilms 32 patients Nasal delivery | 0.9% NaCl CaCl, MgCl and potassium phosphate, 0.21% Na pyruvate 0.06% BAC and no Ethanol. Sinusitis with mucus and biofilms 38 patients Nasal delivery |
|---|---|---|---|---|---|---|
| Percentage decrease in coughing and | 20% | 59 % | 16% | 73% | 88% | 55% |
| Percentage increase in nitric oxide | 28% | 38% | 9% | 38% | 84% | 59% |
| Percentage increase in FEV-1 over baseline | 14% | 21% | 12.4% | 26% | 34% | 26% |
| decrease in sinus biofilms and infections including COVID-19, Flu, pseudomonas | no | no | no | yes | yes | yes |

TABLE IX

| Various concentrations of pyruvate in 0.90% saline with 0.06% BAC and 0.06% IPA or ethanol | 0.0% pyruvate in saline with 0.06% BAC and 0.06% IPA or ethanol | 0.05% pyruvate in saline with 0.06% BAC and 0.06% IPA or ethanol | 0.1% pyruvate in saline with 0.06% BAC and 0.06% IPA or ethanol | 0.21% pyruvate in saline with 0.06% BAC and 0.06% IPA or ethanol | 0.5% pyruvate in saline with 0.06% BAC and 0.06% IPA or ethanol | 2.0% pyruvate in saline with 0.06% BAC and 0.06% IPA or ethanol |
|---|---|---|---|---|---|---|
| Irritation: 1-10 with 1 being very irritating and with10 producing no irritation in the nasal cavity | 4.1 | 4.9 | 6.8 | 9.7 | 8.9 | 7.4 |

TABLE IX-continued

| Various concentrations of pyruvate in 0.90% saline with 0.06% BAC and 0.06% IPA or ethanol | 0.0% pyruvate in saline with 0.06% BAC and 0.06% IPA or ethanol | 0.05% pyruvate in saline with 0.06% BAC and 0.06% IPA or ethanol | 0.1% pyruvate in saline with 0.06% BAC and 0.06% IPA or ethanol | 0.21% pyruvate in saline with 0.06% BAC and 0.06% IPA or ethanol | 0.5% pyruvate in saline with 0.06% BAC and 0.06% IPA or ethanol | 2.0% pyruvate in saline with 0.06% BAC and 0.06% IPA or ethanol |
|---|---|---|---|---|---|---|
| Percentage increase in Nitric oxide over baseline | 0% | 11% | 26% | 56% | 39% | 31% |
| Percentage of ingredients osmotic effect | 1.02% | 1.08% | 1.12% | 1.23% | 1.52% | 3.02% |

Example 2

Idiopathic Pulmonary Fibrosis (IPF) is a chronic progressive lung disorder associated with excessive tissue remodeling, scarring, and fibrosis, which makes the lungs unable to effectively transport oxygen into the bloodstream resulting in decreased forced expiratory volume in the first second ($FEV_1$) and forced vital capacity (FVC) values, decreased $SaO_2$, and a decrease in nitric oxide associated with nasal inflammation that causes congestion and coughing. Inflammatory pathways are upregulated in the nasal epithelium in 80% of patients with IPF, and in patients with Cystic fibrosis the majority of which is caused by infections that produce biofilms and mucus which is part of the etiology of the disease that affects all lung functions and increases coughing. The production of biofilms and mucus reduces the efficacy of nasal and lung medications that cannot penetrate the biofilm. This decrease in nasal nitric oxide causes an increased duration and severity of the sinus and lung infections, an increase in inflammatory cytokines that causes the cytokine storm, reduced sinus and lung capacity and function, lung fibrosis, coughing, dyspnea and hypoxemia. Nasal inflammation induces oxidative stress, decreases lung functions including $FEV_1$ and FVC values, and increases mucus and coughing. A decrease in total lung functions and capacity results in hypoxemia, dyspnea, and poor quality of life, especially sleep disorders. Blockage of nasal nitric oxide by inflammation and biofilms reduces the amount of nitric oxide reaching the lungs as nitric oxide is a bronchodilator, low levels reduce critical lung functions, leading to increased lung and nasal infections, a reduced Sa02 level, reduced $FEV_1$ and FVC levels also leading to mouth breathing and coughing.

The formula listed below contained 0.21% sodium pyruvate, sodium chloride at 0.9%, Benzalkonium chloride 0.06%, and 0.06% isopropanol. The Ph of 7.8. with KH2P04. The placebo is the same formula listed above without sodium pyruvate.

Methods. This was a 21-day double-blinded randomized placebo-controlled Phase III Clinical Trial. 24 saline placebo control patients and 26 N115 treated patients reported baseline coughs per day for one week and then were treated for 21 days while continuing to report daily coughing. Secondary endpoints included examining patients for FEV1, FVC, and FEV1/FVC ratios at baseline and over the course of 21 days. These patients also suffered with sinusitis.

Results: The data from this study demonstrated that coughing episodes per 24 hours were significantly reduced with no exceptions in all sodium pyruvate (N115) treated patients by 38.4% on day 14 and by 73.2% on 22 day of the trial, whereas the placebo treated group reduced coughing by 16.1% on day 22 (p<0.0001). This correlated well with increased FEV1/FVC ratio, which were 27.9% on day 22 with N115 treated patients compared to 2.37% for placebo (p<0.0001). In N115 treated patients at week 2 showed a significant 26.6% improvement in FEV-1 values compared to 6.83% in the placebo group (p=0.0004). Week 3 showed a similar 26.6% mean improvement in the N115 treated group. No patients withdrew from the trial. No mild, moderate, or serious adverse events occurred. No safety or abnormal changes occurred with any vital signs, blood chemistry or hematology.

Conclusions. This randomized placebo controlled double blinded Phase 3 Clinical Trial demonstrated the efficacy of N115 Nasal Spray to clinically and statistically produce a significant decrease in coughing and increase lung functions compared to the saline placebo (0.06% BAC, 0.06% ethanol and 0.90% saline no sodium pyruvate). Overall, patients receiving N115 reported that their breathing was better, their coughing was reduced, and they were able to sleep better, thus improving their quality of life. After day 21, patients discontinued use of the study medication. Patients were contacted by phone for follow up after 3 months. Impressively, patients reported reduced coughing for a mean 38.8 days for N115 compared to only 5.54 days for the placebo (p<0.0001). Patients on N115 also reported a sustained lower number of coughs per day relative to their baseline coughing (−23.7%) compared to the placebo (−11.9%) (p=0.012)). Overall, patients receiving N115 reported that their breathing was better, their coughing was reduced, and they were able to sleep better, thus improving their quality of life. In this 21-day, A double-blinded randomized placebo-controlled Phase 3 Clinical Trial, no patients withdrew from the trial. No mild, moderate, or serious adverse events occurred. No safety or abnormal changes occurred with any vital signs, blood chemistry or hematology.

Example 3

Inhalation of Sodium Pyruvate to Reduce the Symptoms and Severity of Respiratory Diseases Including COVID-19. Phase II/III The formula listed below contained 0.21% sodium pyruvate, sodium chloride at 0.9%, Benzalkonium chloride 0.02%, and 0.02% ethanol (N115 sodium pyruvate formula). And also tested with 0.21% sodium pyruvate, sodium chloride at 0.9%, Benzalkonium chloride 0.06%, and 0.06% ethanol. The Ph 7.8. These patients did not have a secondary bacterial infection neither sinus or lung, that produced biofilms or mucus, just a COVID-19 infection.

This was a phase-2 study. In the first phase, thirty adults with confirmed active COVID19 infections (by qRT-PCR) were randomly, and blindly, assigned to either a saline nasal spray or a saline+sodium pyruvate nasal spray (N115) treatment group. Patients were instructed to use their spray 3× daily for 14 days. Patient's vital signs (BP, SaO$_2$, HR, RR, Temp.) were monitored and nasal swabs tested for SARS-COV-2 levels every 2 days for 14 days. Patients were asked to complete a Daily Symptoms Log every day for 14 days, scoring the symptoms on a Likert scale from 1-10 with 10 representing the most severe symptoms. Symptoms included fatigue, coughing, hypoxemia, congestion, headache and body ache. Patients also recorded their body temperature 2× daily for the 14 days.

This clinical trial was designed to determine the safety and efficacy of N115 against saline in 30 COVID-19 infected patients. Thirty adults with confirmed (positive PCR test) active COVID-19 infections were randomly, and double blindly, assigned to either a saline nasal spray or a saline and 0.21% sodium pyruvate nasal spray (N115) treatment. Patients self-administered the sprays 3× daily for 14 days. Saline is acknowledged (Edenborough ELVIS project) to physically reduce nasal COVID-19 titers by 0.5 logs to 0.7 logs over untreated patients, reduces duration by 2.6 days over untreated controls and reduces mucus and allergens which subsequently reduces congestion, trouble breathing, and sore throats. Therefore, saline is a comparative control, not a true placebo, for this study.

Viral titers in N115 treated patients were lower compared to saline treated patients through day 8 as measured by RT-qPCR from nasal swabs (p<0.0197). N115 Lowered viral titers below 10,000, the value that has been reported to significantly decrease transmission of the virus. The mean day for patients in the N115 treated group to drop below 10,000 viral genome copies as measured by RT-qPCR from nasal swabs was day 6.4 versus day 7.7 for saline vs day 10.3 for untreated controls. N115 (sodium pyruvate), not saline is a cellular metabolite that increases energy to decrease fatigue, coughing and it increases the synthesis of nasal nitric oxide that will increase vasodilation, bronchial dilation and enhance the immune response that increased fever, chills, and body aches numbers over saline for the 14 days, to fight the infection needed to reduce viral genome copies by day 6.4 vs 7.7 for saline.

Patient's vital signs (BP, SaO$_2$, HR, RR, Temp.) were monitored every 2 days for 14 days. Patients were asked to complete a Daily Symptoms Log every day for 14 days, scoring the symptoms on a Likert scale from 1-10 with 10 representing the most severe symptoms. Symptoms included fatigue, coughing/sneezing, hypoxemia, congestion, trouble breathing, headache and body ache. Patients also recorded their body temperature 2× daily for the 14 days. Over the fourteen-day trial, there was no significant change in blood pressure, Heart Rate, Respiratory Rate. We observed similar improvements in patients treated 3× daily with either saline or N115 in SaO$_2$, trouble breathing, and sore throat. However, N115 performed significantly better with reduced coughing/sneezing (p<0.0435) and fatigue (p<0.0001) symptoms over saline and reduced congestion 26% more than saline by day 7. We observed improvements in patients treated 3× daily with either saline or N115 over the 14 days, for fever, body aches, and chills, but conversely, N115 treatment resulted in higher body temperature (Fever, p<0.0030) and higher scores for body aches (p<0.0001), headaches (p<0.0001), and chills (p<0.0001) over saline, due to the effect of sodium pyruvate to enhance the immune system to fight the infection needed to reduce viral genome copies below 10,000 by day 6.4 vs 7.7 for saline, that has been reported to significantly decrease transmission of the virus. No adverse events were reported from the use of either saline or N115 by patients or clinical staff.

Conclusions: In N115 treated 30 COVID-19 infected patients, N115 lowered viral titers below 10,000 by day 6.4, the value that has been reported to significantly decrease transmission of the virus as measured by RT-qPCR from nasal swabs versus day 7.7 for saline vs day 10.3 for untreated controls. N115 also significantly reduced coughing/sneezing (p<0.0435) and fatigue (p<0.0001) symptoms over saline and reduced congestion 26% more than saline by day 7. The reduction of viral titers was due to the ability of sodium pyruvate to increase nasal nitric oxide that kills infections.

In N115 treated COVID-19 infected patients, which produced slight mucus and biofilms from a secondary infection like pneumonia, (N10) did not reduce their viral titers with the N115 (sodium pyruvate) formula, with 0.02% BAC and 0.02% ethanol by 6.4 days rather it took 6.9 days to reduce viral titers under 10,000 (2.8 log reduction) The formula that contained 0.06% BAC and 0.06% ethanol was very effective and lowered viral titers below 1,000 by day 5.1 (5.1 log reduction from baseline placebo) vs 6.4 days, the value that has been reported to significantly decrease transmission of the virus as measured by RT-qPCR from nasal swabs versus day 7.8 for the saline placebo vs day 10.3 for untreated controls. N115 also significantly reduced coughing/sneezing (p<0.0032) and fatigue (p<0.0001) symptoms over saline and reduced congestion 36% more than saline by day 7. The reduction of viral titers was due to the ability of this sodium pyruvate formula to effectively penetrate biofilms and mucus and to increase nasal nitric oxide that kills infections.

Example 4

COVID LONG HAULER TRIAL. Inhalation of Sodium Pyruvate to Reduce the Symptoms and Severity of Respiratory Diseases Including COVID-19. Phase II/III N36 The formula listed below contained 0.21% sodium pyruvate, sodium chloride at 0.90%, and Benzalkonium chloride at 0.02% and 0.02% ethanol. All patients were negative for any nasal infections including COVID-19 and biofilms.

Long haulers without sinusitis, recovering from severe COVID-19 are at serious risk of developing pulmonary fibrosis (10% JAMA). Patients with pulmonary fibrosis have an increased risk and susceptibility to COVID-19 infection, which can reach a mortality rate of 50%. Long Covid patients also have low levels of nasal nitric oxide. N115 significantly reduced coughing/sneezing, increased SaO$_2$ levels (decreased hypoxemia) and improved breathing (dyspnea) in patients with Pulmonary Fibrosis, and there was a statistically and clinically significant improvement in all lung functions, compared to baseline, as determined by changes in Nitric oxide, Sa02, FVC, FEV$_1$, PEF, and FEV-1/FVC ratio from 52% to 86%. This data was submitted to the FDA prior to the testing of long haulers. Studies at NIH have shown that for some people, SARS-COV-2 doesn't completely clear out after acute infection. Scientists have observed signs that the virus may persist in various parts of the body, and many suspect that this lingering virus, or remnants consisting of SARS-COV-2 protein, may be causing Long COVID symptoms in some individuals. Now, in a new study, scientists found that people with Long COVID were twice as likely to have these viral remnants in their blood as people with no lingering symptoms. These remnants when found in the nasal cavity increase inflammation, mucus production and cause a decrease in the synthesis of nitric oxide. Bacterial toxins that can be found in the brain, like pneumolysin produced by *Streptococcus pneumonia*, the epsilon toxin produced by *Clostridium perfringens*, and fibrin produced by the COVID-19 which can leak into the brain and activate microglia the brains immune cells. This activation leads to neurologic symptoms such as brain fog, and difficulty concentrating, Thus, we examined the effects of N115 in 36 patients that were experiencing long-term symptoms after recovering from active COVID-19. "Long-haulers," were monitored for symptoms for one week with no treatment followed by one week with treatment with N115. Patients were not randomized but served as their own negative controls.

Change in the symptoms of Long Hauler COVID-19 patients: During the first seven days, when there was no treatment, patients reported little to no change in symptoms including body ache, headache, coughing/sneezing, and trouble breathing (0 to 1-point improvement on patient logs). However, after N115 treatment for seven days, patients reported a significant 2.2-point improvement (p<0.001) in coughing/sneezing and a 3-point improvement in trouble breathing (p<0.0001). Fatigue, anxiety, loss of taste/smell, congestion, body aches and headaches also showed some improvement, but the changes were not significant due to a lack of power from too few patients presenting with these symptoms enrolling in the study.

Change in body temperature in Long COVID-19 patients: Fever (temperature above 99.5° F.) was not a common symptom and no significant change in body temperature was observed during treatment.

Change in pulse rate in Long Haulers COVID-19 patients: Heart rate remained stable throughout the trial with or without treatment.

Change in blood oxygenation in Long Haulers COVID-19 patients: During the initial 7 days when patients received no treatment, there was a non-significant change in $SaO_2$ of 0.1%. However, immediately after the first dose of N115 was administered on day 7, $SaO_2$ improved by 0.45% from the pretreatment reading on the same day (p<0.001). It continued to improve, and on day 14, after 7 days of N115 treatment, $SaO_2$ levels improved by 1.65% over day 1 and 1.55% over day 7 pretreatment (p<0.0001). Overall, N115 significantly improves respiratory function in as little as 15 minutes with substantial improvement in 7 days compared to no treatment controls. The inhalation of N115 demonstrated its ability to significantly reduce hypoxemia and dyspnea.

Conclusions: In N115 treated Long COVID patients, a significant improvement (p<0.001) in coughing/sneezing and improvement in trouble breathing (p<0.0001) were recorded. Fatigue, anxiety, loss of taste/smell, congestion, body aches and headaches also showed some improvements. However, immediately after the first dose of N115 was administered, $SaO_2$ improved significantly from the pretreatment reading on the same day (p<0.05) and continued to improve by day 14 by 1.65% (p<0.0001). Overall, N115 significantly improves respiratory function in as little as 15 minutes, which is a consequence of increasing the synthesis of nasal nitric oxide.

Example 5

Treatment of patients with pulmonary fibrosis and COPD and IPF with sodium pyruvate (0.21%) in 0.9% saline nasal spray with 0.02% BAC and 0.02% ethanol. These patients did not have nasal infections or biofilms.

Objectives: There have been over 32,381 patient complaints to the FDA from patients with Idiopathic Pulmonary Fibrosis, stating that Rx, OTC, and steroid-based inhalation products, have failed to provide relief from nasal or lung inflammation[a]. This study was designed to determine the effect of inhaled 0.21% sodium pyruvate nasal spray in these patients, with and without their medications, and to determine if the nasal inhalation of sodium pyruvate would have any added benefit to current therapies on nasal inflammation; lung functions, including FVC, FEV1, PEF; and FEV-1/FVC ratios; $SaO_2$: expired NO, and frequency of coughing.

Methods: An initial twenty-one-day sub-chronic clinical trial was conducted that included fifteen patients with Pulmonary Fibrosis (9 with Pulmonary Fibrosis and COPD and 6 with Idiopathic Pulmonary Fibrosis without COPD) that remained on their normal medications, but were also administered the 0.21% sodium pyruvate nasal spray. If the patients were also on nasal sprays as part of their normal therapy, that nasal spray was eliminated. In all 15 patients the test results were compared to their previous three-week screening and baseline data (there current therapies) as the placebo control for each variable including all their lung functions, FEV-1, FVC, PEF, FEV-1/FVC ratios, $SaO_2$, Nitric oxide, coughing rates, nasal inflammation.

Results:

The data from this study showed that coughing episodes per 24 hours, and especially at night, were significantly reduced in all 15 patients on day 8 by 30% (p=0.007) and continued to decrease on day 14 by 55% (p=0.0001) and on the 22 day of the trial, coughing decreased by 59% (p=0.0001). This correlated with a significant (p=0.010) improvement in nasal irritation/erythema with most patients being free of irritation by day 22 (p<0.001); and a significant (p=0.010) increase in the group average expelled NO by day 8.

Unexpectedly a significant (p=0.010) improvement in lung function (breathing) was observed in all patients with Idiopathic Pulmonary Fibrosis without COPD by day eight, increasing to p=0.0005 by day 22 compared to baseline, as determined by changes in FVC, FEV1, PEF, and $FEV_1$/FVC ratios. The improved $FEV_1$/FVC ratio from 52% to 86% was clinically significant and indicated that current therapies in use are inadequate to treat patients with Idiopathic Pulmonary Fibrosis.

The screening data indicate that the 6 IPF patients were not receiving much, if any, benefit from their current therapy. However, they all had significant improvements in breathing at all time periods for FVC, $FEV_1$, and PEF despite the fact that they were all on concomitant standard lung function therapy. Patients #5 and #7 were taking albuterol, a β2-receptor antagonist, and Advair Diskus, a β2-receptor antagonist-steroid combination for rescue; Patient #6 was taking ipratropium-albuterol, a β2-receptor antagonist; and patient #8 was taking albuterol and budesonide/formoterol (Symbicort; a steroid). The sodium pyruvate treatment was able to significantly improve the breathing of these 6 patients, despite 5 of them being on steroid medications.

Following this, five new patients with Pulmonary fibrosis and COPD had their medications removed and were administered only the sodium pyruvate nasal spray solution for three days in order to assess its effect. The data from the three-day trial indicated a statistically and clinically significant immediate average improvement in lung function (breathing), compared to baseline, as determined by changes in FVC, $FEV_1$, PEF, and $FEV_1$/FVC, ratios which persisted throughout the three-day trial. A significant immediate average improvement was also seen in $SaO_2$ levels, compared to baseline, such that all subjects had $SaO_2$ levels of $\geq 97$, which persisted throughout the trial demonstrating the ability of N115 to reduce hypoxemia and dyspnea.

Conclusion: Inhalation of the 0.21% Sodium Pyruvate nasal spray with 0.02% benzalkonium chloride and 0.06% ethanol in 0.9% saline, (N115 is sodium pyruvate in this formula) for 21 days in all patients, demonstrated that coughing was significantly reduced. There was also a significant improvement in nasal irritation/erythema with most patients being free of irritation by day 22, and there was a significant increase in the group average expelled-NO increased during the study. The six patients with Idiopathic Pulmonary Fibrosis patients in this sub-chronic trial demonstrated a significant improvement in lung function (breathing) compared to baseline, as determined by changes in FVC, $FEV_1$, PEF, and $FEV_1$/FVC, ratios. The clinically significant improvement in the FEV-1/FVC ratio 52% to 86% indicated that current therapies in use are inadequate to treat patient with Idiopathic Pulmonary Fibrosis (no COPD component) and that the inhalation of 0.21% (20 mM) sodium pyruvate produced results significantly better to any current therapy in all patients with pulmonary fibrosis. The patients with their regular therapy removed that were treated for three days with only sodium pyruvate nasal spray demonstrated a statistically and clinically significant immediate average improvement in lung function (breathing), compared to baseline, as determined by changes in FVC, $FEV_1$, PEF, and $FEV_1$/FVC, which persisted throughout the three-day trial. A significant immediate average improvement was also seen in $SaO_2$ levels, demonstrating the ability of N115 to reduce hypoxemia and dyspnea. In patients with IPF, but with sinusitis, the above formula was not as effective as the N115 formula with 0.06% BAC and 0.06% ethanol, needed to dissolve biofilms and allow sodium pyruvate to treat nasal cells to increase the synthesis of nitric oxide. See examples 1 and 2.

Example 6

Tissue culture and human clinical studies that demonstrate that lung fibrosis can be reversed using Sodium Pyruvate with the surfactant enhancer ingredients to target Myofibroblasts. The formula did not have BAC or ethanol.

In experiments using lung tissues from 6 patients with pulmonary fibrosis and/or IPF, it was demonstrated that the reversal of lung fibrosis and the underlying cellular mechanisms were affected by the use of the 0.21% sodium pyruvate saline formula with the addition of calcium chloride, magnesium chloride and potassium phosphate (surfactant enhancer ingredients).

Cellular activity was lower in myofibroblast cells within fibrotic regions of human lung tissue from pulmonary fibrosis and/or IPF patients. Myofibroblasts deposit extracellular collagen fiber as part of the fibrosis process. Structural changes to the airway are believed to contribute to an irreversible decrement in lung function in these individuals. Subepithelial deposition of collagen (types I, III, and V) and other extracellular proteins, fibroblast proliferation, mucus hypersecretion, and smooth muscle thickening are all evident in airway remodeling in pulmonary Fibrosis. Other cellular components may not only stimulate differentiation of fibroblasts to myofibroblasts, but also inhibit apoptosis of the myofibroblasts in the lung parenchyma causing extended survival of this population and excessive collagen deposition, which causes fibrosis.

Activation of myofibroblasts apoptosis from lungs of humans with pulmonary Fibrosis, using the 0.21% sodium pyruvate saline nasal spray with the addition of calcium chloride, magnesium chloride and potassium phosphate (surfactant enhancer ingredients) led to lower fibrotic activity, also enhanced the production of new mitochondria, the organelles in cells that produce energy in the myofibroblasts, and it normalized the cells' sensitivity to apoptosis.

The combination of sodium pyruvate and calcium chloride, potassium phosphate and magnesium chloride were synergistic in its ability to increase the incorporation of pyruvate into in myofibroblast cells It enhanced cellular activity and decreased collagen deposition that inhibited fibrosis, specifically measured by changes in sub-epithelial matrix deposition, using histochemical and immunohistochemical staining. In previous studies with rat lungs previously treated with bleomycin, using [2-(14)C] labeled pyruvate; cellular activity and analysis clearly showed that the sodium pyruvate, calcium chloride, potassium phosphate and magnesium chloride formula decreased fibrosis by inhibiting cellular enzymes that increase fibrosis.

Human studies: Nintedanib slows the rate of decline for FVC by 52.3% in 24 weeks compared to the non-treatment group of a 66.7% decline in FVC. It is a pill and has many side effects, especially on the liver. Nintedanib also demonstrated no efficacy in reducing coughing, increasing $SaO_2$, decreasing nasal inflammation, increasing the synthesis of nasal nitric oxide needed for bronchial dilation, enhanced sleeping or apoptosis of myofibroblasts.

Example 7

Pulmonary arterial hypertension (PAH) is a severe disease with a resultant increase of the mean pulmonary arterial pressure, right ventricular hypertrophy and eventual death. Research in recent years has produced various therapeutic options for its clinical management but the high mortality even under treatment remains a big challenge attributed to the complex pathophysiology. Studies from clinical and non-clinical experiments have revealed that the nitric oxide (NO) pathway is one of the key pathways underlying the pathophysiology of PAH. Many of the essential drugs used in the management of PAH act on this pathway highlighting its significant role in PAH. Meanwhile, several novel compounds targeting on NO pathway exhibits great potential to become future therapy medications. Furthermore, the NO pathway is found to interact with other crucial pathways. Understanding such interactions could be helpful in the discovery of new drug that provide better clinical outcomes. A majority of these patients have low levels of nitric oxide. The inhalation of the 0.21% (20 mM) sodium pyruvate formula with lung surfactant ingredients (0.15% calcium chloride, 0.11% magnesium chloride and 0.03% potassium phosphate) in 0.61% sodium chloride (saline) and no 0.06% BAC or 0.06% ethanol, was nebulized in 20 patients that also received the nasal spray used three times a day for a week which contained 0.21% (20 mM) sodium pyruvate formula with lung surfactant ingredients (0.15% calcium chloride, 0.11% magnesium chloride and 0.03% potassium phosphate) in 0.61% sodium chloride (saline) with 0.06% BAC and 0.06% ethanol. This treatment reduced their pulmonary hypertension by 32% (p=0.02) as determined by clinical measurements for FEV-1. FVC, echocardiogram ejection fractions and echocardiography.

Example 8

Treatment of Migraines with the 0.31% sodium pyruvate nasal spray with the 0.06% BAC and 0.06% ethanol formula.

The National Headache Foundation estimates that 28 million Americans suffer from migraines with sinusitis occasionally. More women than men get migraines and a quarter of all women with migraines suffer four or more attacks a month; 35% experience one to four severe attacks a month, and 40% experience one or less than one severe attack a month. Each migraine can last from four hours to three days. People with migraines may inherit the tendency to be affected by certain migraine triggers, such as fatigue, bright lights, stress, oxidative stress, nasal infections, pollen, mold all of which increases the levels of inflammatory cytokines, oxygen radials (hydrogen peroxide and peroxynitrite). A migraine begins when hyperactive nerve cells send out impulses to the blood vessels, causing them to clamp down or constrict, followed by dilation (expanding) and the release of prostaglandins, serotonin, and other inflammatory like oxygen radicals substances that cause the pulsation to be painful. Many migraines seem to be triggered by external factors. Possible triggers include: Emotional stress, sensitivity to specific chemicals and preservatives in foods, caffeine, changing weather conditions, menstrual periods, excessive fatigue, nasal infections, seasonal allergies, oxygen radicals and toxins that trigger an immunological response and changes in normal sleep pattern. Triggers such as pollen, mold, nasal infections which produce oxygen radicals and also cause blood vessels to dilate, which is why you do not want to increase the synthesis of nitric oxide when the patient does not have sinusitis. The use of the 0.31% sodium pyruvate nasal spray in 0.9% saline with 0.06% BAC and 0.06% ethanol relieved migraines and blurred vision and congestion in 9 of the 12 patients tested in less than 2-5 minutes. The other 3 patients had very high thick mucus levels and only responded when N-acetylcysteine was added to the formula. When these same patients tested the 0.21% or higher 0.31% sodium pyruvate formula with the 0.06% BAC and 0.06% ethanol took between 20-40 minutes to relieve the migraine.

Example 9

Alzheimer's and Parkinsons Sinusitis and Oxidative Stress

Among millions of sufferers of chronic rhinosinusitis (CRS), the challenge is not only constantly coping with CRS-related symptoms, such as congested nose, sinus pain, and headaches, but also various complications, such as attention difficulties and possible depression. These complications suggest that neural activity in the central nervous system may be altered in those patients, leading to unexpected conditions, such as neurodegeneration in elderly patients. Recently, some studies linked the presence of CRS, and the production of toxins that can be isolated from brain tissue, and cognitive impairments that could further develop into Alzheimer's disease (AD), dementia and Parkinson's. AD is the leading cause of dementia in the elderly and is characterized by progressive memory loss, cognitive behavioral deficits, and significant personality changes. The microbiome, especially those in the gut or sinuses, has been recognized as a human organ and plays an important role in the development of various conditions, including AD and Parkinsons. However, less attention has been paid to the microbiome in the nasal cavity. Recent analysis has demonstrated that 50% of people with Parkinsons disease are more likely to experience runny nose or rhinorrhea. People with Parkinson's also have a distinct microbiome with higher concentrations of certain bacteria which can lead to neurodegenerative damage and inflammation in the brain which also leads to biofilms and more nasal mucus. Increased nasal inflammatory responses due to CRS may be an initial event that changes local microbiome homeostasis, which may further affect neuronal integrity in the central nervous system resulting in AD. Evidence suggests a potential of β-amyloid deposition starting in olfactory neurons, which is then expanded from the nasal cavity to the central nervous system. Scientists believe that Alzheimer's is caused by the abnormal buildup of proteins in and around the brain cells. In the past, scientists observed that special immune cells in the brain called astrocytes became activated in response to these protein clumps. But the mechanisms by which the astrocytes are able to remove the protein clumps are not well understood. It has been established by our research that sodium pyruvate activates astrocytes to remove excess proteins.

Oxidative stress. The oxidative stress theory, one of the primary etiological theories for Alzheimer disease (AD) and Parkinson's, suggests free radical accumulation as an AD clinical marker. Oxidative stress-derived free radicals can promote the phosphorylation of AB and tau proteins and alter neuronal DNA and RNA. Nitrosative stress, closely associated with oxidative stress, involves the interplay of ROS and reactive nitrogen species formation and scavenging pathways. ROS, including superoxide anion ($O_2^-$), hydrogen peroxide, and hydroxyl radical, can interact with high ROS levels to create a series of potent oxidative free radicals and nitro groups, including pernitrite anion (ONOO—) and peroxynitrite (HOONO). These compounds contribute to the production of 3-nitrotyrosine from various biomolecules (lipids, DNA, RNA, proteins), causing cellular damage or apoptosis-commonly known as nitrosative stress. Its mechanisms leading to cell death include target protein tyrosine nitration, mitochondrial dysfunction, and cell membrane disruption. Peroxynitrite induces cell death, and can influence signal-transduction processes, mitochondrial function and signaling of apoptosis. The formation and reactions of peroxynitrite play a significant role in various diseases. Products of peroxynitrite reactions with macromolecules have been detected in several pathophysiological conditions, including vascular diseases, ischemia-reperfusion injury, circulatory shock, inflammation, pain and neurodegeneration especially in Alzheimer's. In these conditions, pharmacological inhibition of the formation or action of peroxynitrite was shown to be of benefit. Pyruvate a strong antioxidant reacts directly with peroxynitrite to eliminate it.

Bacterial, viral and fungal toxins produced in sinusitis. *Pseudomonas aeruginosa* produces a large number of extracellular toxins, which include phytotoxic factor, pigments, hydrocyanic acid, proteolytic enzymes, phospholipase, enterotoxin, exotoxin, and slime. The most important factor in the pathogenicity of *P. aeruginosa* is the elaboration of a group of protein exotoxins. These exotoxins can produce leukopenia, acidosis, circulatory collapse, necrosis of liver, pulmonary edema, hemorrhage, and tubular necrosis of kidneys and brain damage. Passive administration of antitoxic sera against these exotoxins is able to protect against lethal infections with *P. aeruginosa* in the absence of antibody against the cellular antigens. The proteolytic enzymes produced by *P. aeruginosa* are responsible for the hemorrhagic and necrotic changes in the nasal cavity, as well as destruction of cornea in eye infections. Phospholipase may be responsible for destruction of pulmonary surfactant with resultant atelectasis. This effect, together with the necrosis of lung tissue, may be important in the pathogenesis of the damage to lungs in the patients with pneumonia due to *Pseudomonas*. Strains of *P. aeruginosa* are capable of producing an enterotoxin that is probably responsible for decreasing the synthesis of nitric oxide. Many of these toxins can relocate to the brain to cause Alzheimer's and Parkinson's. Toxic proteases from bacteria called gingipains were identified in the brain of Alzheimer's patients and levels correlated with the tau and ubiquitin pathology. Oral *P. gingivitis* infections resulted in brain colonization in increased production amyloid plaques. These same bacterium and toxins were found in patients with Parkinsons. These toxins destroy dopamine synthesizing cells. Bacterial toxins that can be found in the brain, like pneumolysin produced by *Streptococcus pneumonia*, the epsilon toxin produced by *Clostridium perfringens*, and fibrin produced by the COVID-19 which can leak into the brain and activate microglia the brains immune cells. This activation leads to neurologic symptoms such as brain fog, and difficulty concentrating. Fungal toxins produce toxins like ochratoxin A that can cross the blood brain barrier causing neurotoxicity and triggering inflammation and disrupting synaptic transmission within the brain.

Treatment to eliminate sinusitis and eliminate toxins. Alzheimer's patients produce brain nitric oxide needed for normal brain function. By using the combination of oral pyruvate with the combination of the nasal spray in 13 AD patients, it increased lung functions and SaO2 because many AD patients have persistent sinusitis which produces biofilms and mucus that block sodium pyruvate form increasing the synthesis of nitric oxide and protecting nitric oxide from oxygen radicals to increase and protect lung functions and SaO2. The use of the nasal spray with 0.21% sodium pyruvate and 0.06% BAC and 0.06% ethanol increased both lung functions, Sao2 and levels of nitric oxide. The use of the nasal spray along with treating the patients with 2 gram of calcium pyruvate three times daily, as a pill increased both nasal and lung nitric oxide and increased nitric oxide and SaO2 throughout the body as measured from blood samples. Pyruvate can be administered by IV at 2.1 grams/ 70 kg person delivered in 1000 ml saline solution or 2.1 mg/ml for a 70 kg person. Of the 13 patients treated, 9 had Alzheimer's that included two with dementia and 4 with Parkinson's, the treatment increased cognitive functions as outlined below by over 45% over their own baseline measurements. 3 of the 4 Parkinson's patients responded well to the treatment, with decreased tremors, and increased dopamine level by 27%, and also eliminated sinusitis and the toxin sinusitis produces that can affect the brain tissue. Blood levels of toxins were eliminated after 21 days of treatment and the sinusitis infections were eliminated as demonstrated by nasal swab bacteria, fungal or viral analysis.

Table X. The use of a nasal spray with 0.21% sodium pyruvate 0.9% saline formula with 0.06% Benzalkonium chloride (BAC) and 0.06% ethanol against placebo for 21 days in patients with a lung disease and sinus bacterial infections and biofilms, including viral or fungal sinusitis infections, *pseudomonas* especially in Alzheimer's and Parkinson's patients. Overall rating was 1-10 with 1 being the most negative and 10 being the best result for reduction of mucus. Please note that higher concentrations of BAC and IPA were just as effective as the 0.06% level for both. 0.1% for BAC and ethanol was effective as was 0.2% of BAC and IPA. The least irritating formula was the 0.06% of the BAC and 0.06% ethanol. The increased synthesis of Nitric oxide increases its mucolytic and bronchial dilator effect. It is an effective short-acting bronchodilator. This effect contributes to the removal of secretions and maintains airway functions. Nitric oxide has also been seen to control ciliary beat frequency in the airways to remove mucus. The increased synthesis of nitric oxide reduced bacterial (−5.6 logs mostly *pseudomonas* and other bacteria strains) in 13 Alzheimer's patients and in 6 Parkinson's patients.

TABLE X

| pyruvate in saline with BAC and ethanol | Percentage Increase in FEV-1 over (baseline) at day zero | Percentage increase of Nitric Oxide over baseline | Nasal inflammation 1-10 | Relief of coughing percentage decrease | Percentage Increase in SaO2 over baseline, decrease in hypoxemia | Averaged Reduction in bacterial logs over baseline |
|---|---|---|---|---|---|---|
| nasal infections | 24.0 | 49.0% | 8.4 | 92 | 7 | 5.55 |

Preliminary Cognitive Testing: Three-Word Recall, "Mini-Cog" and Coin Counting

The following two tests can help gauge memory function when patients express concern. The tests also may help identify patients who need more thorough evaluation. All of these tests are relatively free of influence by educational level:

a Three-Word Delayed Recall Exercise

The patient is told to remember three words, these being three common nouns, such as horse, pencil and rose. The patient was then asked to repeat them. About five minutes later, the patient was then asked to recall them.

Individuals without impairment should be able to remember all three words, especially with such prompts as, "The first word was the name of an animal."

Remembering only one or two words indicates a need for further evaluation.

2. The "Mini-Cog" Test, Combining Three-Word Recall with Clock-Drawing

Three simple nouns were given, and the patient was asked to repeat them.

The patient was then asked to draw the face of a clock on a sheet of paper, showing the time as 10 minutes past 11.

After the clock has been drawn, ask the patient to repeat the three words.

Patients who remember all three words have no dementia.

Patients who remember none of the words should receive further evaluation.

If the patient remembers one or two words, the physician should refer to the score on the clock drawing to help interpret this result.

normal clock=non-demented abnormal clock=further evaluation needed,

Patients who recall all three words but have a problem with the clock may also require further evaluation.

More about clock-drawing and scoring

When stating the time to be shown on the clock, avoid referring to the "hands" of the clock to avoid prompting. Rather, say "Show the time as 10 past 11."

"10 past 11" tests the ability to translate "10 past" into the right numerical value.

It also requires the use of both halves of the clock face.

There are several scoring systems. A simple one is based on four points, with a lower score suggesting further evaluation.

One point is given for drawing a closed circle. Some clinicians prefer to give patients a pre-drawn circle, so that any accidental distortions in shape do not affect the placement of the numbers.

One point is awarded for including the 12 correct numbers.

One point is given for putting the numbers in the correct position.

One point is awarded for drawing the hands to show the correct time.

Using the above-described tests, on these Alzheimer's patient, improved cognitive function moderately, over base scores, with the patient being able to increase his scores by 34%. When pyruvate was administered by itself their scores increased by 45% over base measurements. The combination of the nasal spray and pyruvate increased their cognitive abilities to nearly 48%, showing that pyruvate oral or IV and the nasal spray are synergistic p=0.002. In six Alzheimer patients, C13 labeled sodium pyruvate given by IV was found to activates astrocytes that removed excess proteins surrounding in brain cells, helping increase cognitive function in these patients.

Example 10

Epinephrine nasal spray which is now FDA approved for the treatment of anaphylaxis, causes side effects: throat irritation, tingling nose, nasal discomfort, sneezing, itchy nose, nasal congestion or runny nose and headaches. In clinical studies with Epinephrine in 19 patients and many other drugs including insulin, cancer drugs, steroids, antimicrobials, antivirals, the addition of sodium pyruvate to the nasal spray eliminates tingling nose, nasal discomfort, sneezing, itchy nose, nasal congestion or runny nose and headaches, as it did in our long Covid human phase 3 clinical. This formula allows the drugs to penetrate biofilms and mucus to reach the targeted nasal cells.

In all the formulas above that contain the 0.21% sodium pyruvate, in 0.9% saline and 0.06% or higher levels of BAC and 0.06% ethanol, eliminated the biofilm and mucus allowing sodium pyruvate to reach nasal cells and significantly increased FEV-1 values (13%), increase the production nitric oxide (14%), Sa02 values, as well as a significant reduction of nasal inflammation caused by inflammatory cytokines and significantly decrease coughing (23%) and allowing Epinephrine to reach nasal cells to produce the maximum efficacy possible.

Example 11

Oxymetazoline nasal spray once daily induces rebound swelling and nasal hyperreactivity that can be reversed with the addition of pyruvate. Ohio State University medical center 2001.

A randomized double-blind parallel study with 90 healthy patients was performed to study the effect of oxymetazoline nasal spray and the development of rhinitis medicamentosa, that occurs, with and without and addition of pyruvate, a well-known antioxidant and anti-inflammatory agent. 45 subjects were treated with the oxymetazoline nasal spray once daily for 30 days at night and placebo in the morning and at noon. The other 45 patients were treated with the oxymetazoline nasal spray containing 0.21% of sodium pyruvate once daily at night and placebo in the morning and at noon. The mucosal surface positions were determined with rhinostereometry, before and after treatment, followed by histamine challenge tests. In the morning and the evening just before use of the nasal spray, symptoms of nasal stuffiness were evaluated on visual analogue scales (0-100). Rebound swelling and nasal stuffiness occurred only in the oxymetazoline group without the addition of the pyruvate to the formula after 30 days of treatment. In the group receiving oxymetazoline nasal spray once daily at night, the mean rebound swelling was 1.1 mm (p<0.02) and the estimated mean symptom score for nasal stuffiness in the evening was 39 (p<0.03). The group receiving oxymetazoline with pyruvate, nasal spray once daily at night, the mean rebound swelling was 0.2 mm (p<0.01) and the estimated mean symptom score for nasal stuffiness in the evening was 3 (p<0.03). The oxymetazoline demonstrated an increase in histamine sensitivity without pyruvate and indicated nasal hyperreactivity. It is concluded that the risk of developing rebound swelling and nasal hyperreactivity remains, with oxymetazoline nasal spray when it is used once a day for 30 days. The addition of pyruvate to the oxymetazoline formula eliminated rebound swelling and nasal stuffiness.

Background

In most countries, the use of topical nasal decongestants is limited to a maximum of 10 days because of the risk of developing rebound mucosal swelling and rhinitis medicamentosa.

Objectives: To determine whether topical nasal decongestants can be safely used for 30 days in patients with chronic inflammation of the nasal mucosa. Design Double-blind, randomized, controlled, parallel study.

Patients

Ninety patients with vasomotor rhinitis, 56 women and 34 men (mean age, 38 years), entered the trial. Most of them had nasal blockage as their main symptom, but, in some patients, secretions and/or sneezing was the dominating symptom. Twenty-nine patients had used nasal corticosteroids before entering the trial, but no one was allowed to use any medication for nasal symptoms for 1 month before entering the study. On rhinoscopy, no signs of a structural basis for the nasal symptoms were noted.

Forty-five patients received oxymetazoline hydrochloride (0.5 mg/mL) nasal spray containing the preservative benzalkonium chloride (0.1 mg/mL), and the other Forty Five were treated with oxymetazoline nasal spray with benzalkonium chloride and sodium pyruvate. Before and after the treatment, recordings of the nasal mucosa and minimal cross-sectional area were made with rhinostereometry and acoustic rhinometry, followed by histamine hydrochloride challenge tests. Symptoms of nasal stuffiness were estimated on visual analog scales (0-100) in the morning and the evening, just before the nasal spray was used. Throughout the 30 days of medication, each subject filled in a diary card in the morning and the evening, just before using the nasal spray. Nasal stuffiness was estimated on a visual analog scale (0-100). The scale ranged from 0 (nose completely clear) to 100 (nose completely blocked). Informed consent was obtained before any procedure was performed.

STUDY DRUGS Both groups sprayed 0.1 mL of the substances into each nostril 3 times daily. One group was randomized to treatment with oxymetazoline hydrochloride (0.5 mg/mL) nasal spray without pyruvate, and the other group received oxymetazoline hydrochloride (0.5 mg/mL)

nasal spray with pyruvate 20 mM. The study drugs were all in a new type of nasal spray bottle shown to withstand bacterial contamination.

MEASURING METHODS The nasal mucosal swelling was recorded with rhinostereometry and acoustic rhinometry. Rhinostereometry is an optical, direct, noninvasive method for measuring nasal mucosal swelling with a high degree of accuracy. A surgical microscope is placed on a micrometer table fixed to a frame. The microscope is movable in 3 angular directions, establishing a 3-dimensional coordinate system. The subject is fixed to the apparatus by a plastic, individually made tooth splint. The eyepiece has a horizontal millimeter scale. The nasal cavity is viewed through the eyepiece. Since the microscope has a small depth of focus, changes in the position of the mucosal surface of the medial side of the head of the inferior concha are registered in the plane of focus along the millimeter scale. The accuracy of the method is 0.2 mm. Acoustic rhinometry produces an acoustic pulse that enters the nose via a tube equipped with a nose adapter tightly placed in the nostril. Changes in the cross-sectional area are digitized by a computer, and numerical values of the cross-sectional area are recorded. The minimal cross-sectional area, MCA 2, is the cross-sectional area between the anterior portions of the inferior concha and the septum. The apparatus used in this study was a RHIN 2100 (SR Electronics APS, Lynge, Denmark).

Rhino Stereometric Measurements

In the group receiving oxymetazoline without pyruvate, the mean mucosal swelling after histamine hydrochloride challenge before treatment was 1.4 mm with a dose of 1 mg/mL, 1.8 mm with 2 mg/mL, and 2.2 mm with 4 mg/mL. After 30 days of treatment with oxymetazoline without pyruvate, the corresponding values for mucosal swelling was 1.1 mm with a dose of 0.5 mg/mL of oxymetazoline. In the group receiving oxymetazoline with pyruvate, the mean mucosal swelling after histamine hydrochloride challenge before treatment was 1.6 mm with a dose of 1 mg/mL, 1.9 mm with 2 mg/mL, and 2.0 mm with 4 mg/mL. After 30 days of treatment, the corresponding values for mucosal swelling was 0.2 mm with a dose of 0.5 mg/ml of oxymetazoline in the 20 mM pyruvate solution.

Results: All patients completed the study. However, because of technical difficulties, the Rhino stereometric baseline values are missing in 8 subjects and the corresponding measurements with acoustic rhinometry are missing in 11 other subjects. Since all subjects had complete measurements with at least 1 of the objective methods, no patient was excluded. No rebound swelling was found after the 30-day treatment in the group treated with oxymetazoline nasal spray with sodium pyruvate. Rebound swelling was found in the group treated oxymetazoline hydrochloride (0.5 mg/mL) nasal spray without sodium pyruvate. In the group receiving oxymetazoline and sodium pyruvate, but not in the other group, the histamine sensitivity was significantly reduced after treatment (P<0.001).

Conclusions: It is safe to use topical nasal oxymetazoline with pyruvate for 30 days in patients with vasomotor rhinitis. The pronounced nasal vasoconstriction induced by topical nasal decongestants may be followed by rebound vasodilatation and stuffiness. This is especially likely after long-term use of these drugs. The patient may then become uncertain as to whether congestion is still being caused by the nasal disease or by rebound congestion. The stuffiness is relieved by additional doses of the vasoconstrictor eventually in larger doses, i.e., tolerance. Thus, the patient becomes increasingly dependent on the topical decongestant and a vicious circle is established with long-term daily overuse. This phenomenon is called rhinitis medicamentosa (RM), when the topical decongestants contained ephedrine hydrochloride and RM was a common problem. With modern vasoconstrictors, such as oxymetazoline hydrochloride and xylometazoline hydrochloride, the risk of developing RM and tolerance has been considered to be much smaller or even nonexistent. However, recent studies have shown that overuse of these drugs also results in rebound congestion and histological changes in the nasal mucosa. No other drugs are more effective than topical nasal α2-agonists for relieving nasal stuffiness. Oxymetazoline produces immediate, powerful, long-lasting decongestion, and therefore it is clinically important to establish for how long these drugs may safely be used without risking the development of RM. In the present study, we therefore used patients with chronic untreated rhinitis.

Rhinitis medicamentosa is a condition characterized by nasal congestion that occurs due to the overuse of topical decongestants, particularly intranasal sprays. This condition, also known as rebound rhinitis, can lead to chronic symptoms if the decongestants are used for longer than the recommended duration of 3-5 days. Symptoms may include persistent nasal congestion and sneezing, and in some cases, it can result in complications such as chronic sinusitis. Treatment typically involves discontinuing the use of the offending medication and may require alternative therapies to manage symptoms. When chronic sinusitis produces a biofilm, the use of the 0.21% sodium pyruvate nasal spray in 0.9% saline with 0.06% BAC and 0.06% ethanol significantly decreased nasal congestion and rebound effects of oxymetazoline in 9 of the 12 patients tested. In the group receiving oxymetazoline nasal spray without pyruvate, but with 0.9% saline with 0.06% BAC and 0.06% ethanol once daily at night, the mean rebound swelling was 2.0 mm (p<0.01) and the estimated mean symptom score for nasal stuffiness in the evening was 47 (p<0.02). The group receiving oxymetazoline with pyruvate, nasal spray with 0.9% saline with 0.06% BAC and 0.06% ethanol, once daily at night, the mean rebound swelling was 0.3 mm (p<0.02) and the estimated mean symptom score for nasal stuffiness in the evening was 12 (p<0.003) statistically significant results. To remain isotonic the total amount of ingredients should be isotonic (0.90% to 0.95%). As an example, 0.01% of calcium chloride. 0.01% magnesium chloride and 0.03% of potassium phosphate were added to 0.9% saline with the 0.21% pyruvate to give you a 1.16% total salt solution which is isotonic. If you use the 0.15% calcium chloride, with 0.11% magnesium chloride with 0.03% potassium phosphate, with 0.21% sodium pyruvate the saline must be reduced to 0.45% to be in the isotonic range. The amount of each ingredient is dependent on the severity of the lung or sinus disease. Magnesium chloride has anti-inflammatory to reduce sinus swelling.

Oxymetazoline causes rebound, because it inhibits the synthesis of nitric oxide, which increases the level of infections and the production of biofilms and mucus, which blocks the efficacy of oxymetazoline causing rebound. Oxymetazoline cannot penetrate biofilms or mucus. Pyruvate brings the level of Nitric oxide to normal levels to kill infections increasing the efficacy of oxymetazoline and reduces or eliminates the rebound effect.

Example 12

Coughing Reflex Caused by Inflammatory Cytokines and Toxins

Chronic coughing reflex is caused by irritation from inflammatory cytokines and toxins to the receptors in the tracheobronchial tree. Impulses travel up via the glossopharyngeal and Vagus nerve to produce chronic cough or enhanced cough responsiveness. The Vagus nerve is primarily responsible for the coughing reflex, specifically the sensory fibers within the Vagus nerve that innervate the airways and throat to trigger the cough reflex stimulated by irritating particles.

This was a double blinded placebo-controlled study with 20 patients with chronic coughing reflex, that was not treatable with current therapies. Ten patients were treated with the placebo control, and ten patients were treated with N115 for 21 days. Eligible patients were those with a clinical diagnosis of moderate to severe coughing and a stable pulmonary disease status. Subjects were excluded if: they had clinically significant cardiac disease including uncontrolled congestive heart failure and unstable angina; were pregnant or were females of child bearing age not on adequate contraception; were Lactating females; were receiving systemic corticosteroid treatment within one month of the Screening Visit; they had received inhaled corticosteroid treatment within 15 days of Screening Visit; were hospitalized within the last 6 months prior to the Screening Visit due to acute exacerbation of an airway disease; they were on escalating dose of immunotherapy; they had taken vitamins with anti-oxidants or anti-inflammatory properties, prior to the screening Visit.

The patients were further instructed to continue to administer their usual medication, except for any inhaled corticosteroid and systemic steroids during the trial period. The only restriction was that they had to withhold taking OTC nasal sprays that included oxymetazoline, Albuterol and Ipratropium, and beverages that contain caffeine (e.g. coffee, tea, cola, energy drinks, etc.) for 6 hours; Formoterol and Salmeterol for 12 hours; and Tiotropium for 24 hours, prior to all clinic visits. All these patients had sinusitis caused by bacterial or viral infections. Microbial analysis revealed 40% were infected with a *pseudomonas* infection. Strains of *P. aeruginosa* are capable of producing an enterotoxin that is probably responsible for decreasing the synthesis of nitric oxide, and damage to the coughing nerve. Many of these toxins can also relocate to the brain to cause Alzheimer's and Parkinson's. Toxic proteases from bacteria called gingipains were identified in the nasal cavity as a possible cause of Chronic coughing reflex which is caused by irritation to the nerve receptors. Bacterial toxins that can be found in the nasal cavity, like pneumolysin produced by *Streptococcus pneumonia*, the epsilon toxin produced by *Clostridium perfringens*, and fibrin produced by the COVID-19 activate white blood cells to activate other immune cells to increase inflammatory cytokine that attack and cause irritation to nerve receptors, thus increasing the cough reflex. Fungal toxins produce toxins like ochratoxin A that can cause neurotoxicity and triggering inflammation.

To measure inflammatory cytokines nasal lavage samples were measured by multiplex bead-based assay and by enzyme linked immunosorbent assay (Elisa) in 20 patients. When measured, the 0.21% sodium pyruvate formula with 0.06% BAC and 0.06% ethanol, lowered TNF-alpha by 90%, interleukin-1 beta by 87%, interleukin-8 by 93%, interleukin 10 and 6 by 74% and interferon-gamma by 69% at the end of the 21 day testing period, against day zero, nontreatment, which are primarily associated with causing coughing by triggering inflammation in the airway, which can sensitize nerve ending and lead to a cough reflex. N115 eliminated the inflammatory response that stimulate cough receptors and sensitizes the nerve ending and leads to a cough reflex. Coughing was reduced by 81%.

Analysis comparison of day 0 with no treatment to 21 days of Treatment with 0.21% pyruvate in 0.90% saline with 0.06% BAC and 0.06% ethanol or placebo. Percentage increase or decrease was determined from baseline day 0 with no treatment and compared to the 21-day period of treatment with either pyruvate or placebo (0.90% saline with 0.06% BAC and 0.06% ethanol) Sodium pyruvate has previously been shown to be an effective anti-oxidant and anti-inflammatory agent. These bioactive characteristics were confirmed in this Phase 2 study. There was a clinically significant difference in the decrease of the inflammatory cytokine/chemokine when sodium pyruvate was administered for 21 days, when compared to sodium chloride placebo therapy at the same time period.

TABLE XI

|  | TNF alpha | Inter-leukin 1 | Inter-leukin 8 | Inter-leukin 6 | Inter-leukin 10 | Inter-feron Gamma |
|---|---|---|---|---|---|---|
| Saline placebo | +11 | +6 | +19 | −12 | +24 | +43 |
| Pyruvate | −90% | −87% | −93% | −74% | −74% | −69% |
| P values | 0.001 | 0.0023 | 0.00045 | 0.0001 | 0.002 | 0.003 |

Example 13 Eliminating Sneezing

Many things cause sneezing including allergies to mold, dust, viral infections, steroids, etc. When sneezing your body releases hormones, inflammatory cytokines, including histamines. The cytokines listed in example 12 will increase sneezing. 23 patients that are allergic to mold and dust were exposed to dust and the sneezing lasted for over one hour. When these same patients were exposed to dust again on the next day, but used the nasal spray with 0.21% sodium pyruvate formula with 0.06% BAC and 0.06% ethanol the sneezing stopped within one minute.

Example 14

Various formula and disease treatments. Each formula signally or in combination can treat various lung and sinus diseases including infections. The best formula to treat sinusitis and dissolve mucus and biofilms to increase nasal nitric oxide to kill infections is number 4 and 5. Numbers 1 and 2 do not contain BAC or ethanol to eliminate mucus and biofilms, thus allowing sodium pyruvate to reach cells that synthesize nitric oxide. Formula number 3 is for patients with allergic rhinitis, colds, flu and COVID-19, but without sinusitis or infections. The OTC formula has 0.45% saline with 0.15% to 0.31% sodium pyruvate and 0.02% benzalkonium chloride with 0.02% ethanol, to treat patients with light seasonal allergies. This formula is hypotonic and helps transport sodium pyruvate into nasal cells to treat congestion, inflammation and increase the synthesis of nitric oxide to increase all lung functions including FEV-1 and SaO2 levels. It will not remove mucus or dissolve biofilms and will help with coughing.

Effect of Low levels of nasal nitric oxide:

1. Blurred vision, confusion, dizziness, and lightheadedness when getting up suddenly from a lying or sitting position.
2. Irritation of the lungs and respiratory tract, leading to symptoms such as cough and difficulty breathing.
3. Increased fatigue and weakness due to low nitric oxide levels.

1) Oral nebulized with 0.015% to 0.21% sodium pyruvate in 0.9% saline to decrease lung inflammation, coughing, increase all lung functions and increase lung nitric oxide levels in COPD or other similar lung diseases. No lung surfactants enhancers and no BAC (benzalkonium chloride) or ethanol. Used in 6 human clinicals. See Table 8

2) Oral nebulized with 0.015% to 0.21% sodium pyruvate in 0.61% to 0.9% saline for apoptosis of myofibroblasts and to increase lung surfactants to enhance easier breathing, decrease lung inflammation, coughing, increase all lung functions and increase lung nitric oxide levels in COPD or other similar lung diseases The inhalation of the 0.015% to 0.21% sodium pyruvate formula with lung surfactant ingredients (0.015% to 0.15% calcium chloride, 0.011% to 0.11% magnesium chloride and 0.03% potassium phosphate) in 0.61% to 0.9% sodium chloride (saline) and no BAC and no ethanol or IPA. The percentage of ingredients depends on the severity of the lung disease i.e. COPD, interstitial lung disease like Idiopathic pulmonary fibrosis or Cystic fibrosis. To remain isotonic the total amount of ingredients should be isotonic (0.95% to 0.95%). As an example, 0.01% of calcium chloride, 0.01% magnesium chloride and 0.03% of potassium phosphate were added to 0.9% saline with the 0.21% pyruvate to give you a 1.16% total salt solution which is isotonic. If you use the 0.15% calcium chloride, with 0.11% magnesium chloride with 0.03% potassium phosphate, with 0.21% sodium pyruvate the saline must be reduced to 0.45% to be in the isotonic range. The amount of each ingredient is dependent on the severity of the lung or sinus disease. See table 8 and example 6

3) Nasal spray with 0.31% to 0.21% sodium pyruvate with 0.45% to 0.9% saline with 0.02% BAC and with or without 0.02% ethanol or isopropanol is used to decrease allergic rhinitis, congestion, coughing, migraines, nasal and lung inflammation and to increase all sinus and lung functions and increase the synthesis of nitric oxide, in patients with no sinusitis or infections or biofilms. If you use the 0.15% calcium chloride, with 0.11% magnesium chloride with 0.03% potassium phosphate, with 0.21% sodium pyruvate, the saline must be reduced to 0.45% to be in the isotonic range. This formula can be used with steroids, oxymethoziline and many other drugs listed in this patent sections 31-44. See Tables 1, 7, 8 and examples 1, 5, 8, 10, 11

4) Nasal spray with 0.21% sodium pyruvate with 0.9% saline with 0.06% to 0.1% BAC and 0.06% to 0.1% ethanol or IPA to treat sinusitis or infections with biofilms and mucus in IPF patients, Alzheimer's and Parkinson's or any patient with sinusitis. This formula eliminates COVID-19 and other viral, bacterial and fungal infections and their biofilms, mucus and toxins by increasing the synthesis of nitric oxide, see table 1-7, 8, and 10 and examples 1, 2, 3, 4, 9, and 10, 5) Nasal spray with 0.015% to 2% sodium pyruvate in 0.55% to 0.9% saline for apoptosis of myofibroblasts and to increase lung surfactants to enhance easier breathing, in patients with pulmonary hypertension to decrease allergic rhinitis, congestion, coughing, migraines, nasal and lung inflammation and to increase all lung functions and increase the synthesis of nitric oxide, in patients with sinusitis infections, to kill infections. The inhalation of the 0.015% to 0.21% sodium pyruvate formula with lung surfactant ingredients (0.015% to 0.15% calcium chloride, 0.011% to 0.11% magnesium chloride and 0.03% potassium phosphate) in 0.55% to 0.9% sodium chloride (saline) and 0.06% to 0.1% BAC and 0.06% to 0.1% ethanol or IPA. Isopropanol is a little more irritating, but reduces coughing more than 10% over ethanol. The percentage of ingredients depends on the severity of the sinus and lung disease i.e. COPD, interstitial lung disease like IPF of Cystic fibrosis, pulmonary hypertension and sinusitis. To remain isotonic the total amount of ingredients should be isotonic (0.95% to 1.31%). As an example, 0.015% of calcium chloride, 0.011% magnesium chloride and 0.03% of potassium phosphate were added to 0.9% saline with the 0.21% pyruvate and 0.06% BAC and 0.06% ethanol, to give you a 1.28% total salt solution which is isotonic. If you use the 0.15% calcium chloride, with 0.11% magnesium chloride with 0.03% potassium phosphate, with 0.21% sodium pyruvate with 0.06% BAC and 0.06% ethanol, the saline must be reduced to 0.55% to be in the isotonic range of 1.17%. The amount of each ingredient is dependent on the severity of the lung or sinus disease. See table 8 and example 6, 7 and 8

6) Combination of number #2 and #4 to treat patients with idiopathic pulmonary fibrosis (IPF) with sinusitis infections, biofilms and lung fibrosis. This combination was synergistic in treating these diseases.

7) The Power of Multi-Ingredient Nasal Sprays: Compounded nasal sprays can be prepared and can include a combination of anti-inflammatory, anti-infective, antifungal agents, and biofilm disruptors. This unique formulation targets not just the symptoms but also the underlying pathogens and mechanisms contributing to serious and rare chronic sinusitis. To the Nasal spray with 0.21% sodium pyruvate with 0.9% saline with 0.06% to 0.1% BAC and 0.06% to 0.1% ethanol or IPA you can also add the following ingredients when needed in severe cases. In the testing of 2% of patients with severe sinusitis caused by *Staphylococcus aureus, aspergillus* or *candida*, these ingredients were needed to eliminate the infections quicker.

1. Anti-Infective Agents:
   Mupirocin: Effective against Gram-positive bacteria, including *Staphylococcus aureus.*
   Vancomycin: Targets resistant bacterial strains such as MRSA (methicillin-resistant *Staphylococcus aureus*).
   Tobramycin: A potent aminoglycoside effective against Gram-negative bacteria, often used in cases of *Pseudomonas* infections.

2. Antifungal Agents:
   Amphotericin B or Voriconazole: Address fungal pathogens like *Aspergillus* or *Candida*, which are common in some chronic sinusitis patients.

3. Biofilm Disruptors:

EDTA (Ethylenediaminetetraacetic acid): Breaks down biofilms, the protective barriers formed by bacteria and fungi, which often render standard treatments ineffective. By disrupting biofilms, EDTA allows anti-infective agents to penetrate and eradicate the pathogens more effectively.

What is claimed is:

1. A composition useful for delivering sodium pyruvate and other drugs through biofilms and mucus barriers to stimulate and increase the synthesis of nasal nitric oxide, that will reduce viral and bacterial replication, duration, spread and counts to reduce the severity of infections, to increase lung and sinus functions, reduce coughing, sneezing, inflammatory cytokines and toxins that effect the Vagus nerve, caused by viruses such as COVID-19 and flu in patients susceptible to these infections, including patients with hypoxemia, asthma, chronic obstructive pulmonary disease, cystic fibrosis, diabetics, long COVID, interstitial lung disease, pulmonary fibrosis, idiopathic pulmonary fibrosis, rhinitis medicamentosa also known as rebound rhinitis, allergic rhinitis, congestion, rebound effects of oxymetazoline, seasonal allergies, sinusitis, with migraines, Alzheimer's, Parkinsons and pulmonary hypertension which comprises the following constituents:

a) sodium pyruvate;

b) sodium chloride;

c) benzalkonium chloride;

d) an alcohol selected from: ethanol, isopropanol, methyl alcohol or phenylethyl alcohol; and, e) an aqueous carrier;

wherein said composition contains the following amounts of said constituents: sodium pyruvate ranges from about 0.01% to 1%, sodium chloride ranges from 0.45% to 0.93%; benzalkonium chloride ranges from 0.01% to about 0.2% and alcohol ranges from 0.01% to about 0.2%, balance is said aqueous carrier, all percentages by weight.

2. The composition of claim 1 wherein said sodium chloride ranges from 0.6% to 0.93% by weight, and is in a saline solution with said aqueous carrier.

3. The composition of claim 1 wherein said benzalkonium chloride ranges from 0.04% to about 0.1% and alcohol ranges from 0.04% to about 0.1%, by weight.

4. The composition of claim 1 wherein said benzalkonium chloride content is about 0.06% and said alcohol content is about 0.06%, by weight.

5. The composition of claim 1 wherein said alcohol is ethanol.

6. The composition of claim 1 wherein said alcohol is isopropanol.

7. The composition of claim 1 wherein said alcohol is selected from the group consisting of ethanol, isopropanol, and combinations thereof.

8. The composition of claim 1 wherein said aqueous carrier is water selected from the group consisting of purified water and distilled water.

9. The composition of claim 1 wherein said composition contains the following amounts of said constituents: sodium chloride at about 0.9%; sodium pyruvate at about 0.21%, benzalkonium chloride at about 0.06% and alcohol at about 0.06%, all by weight.

10. A method for delivering sodium pyruvate and other drugs through biofilms and mucus barriers to stimulate and increase the synthesis of nasal nitric oxide, that will reduce viral and bacterial replication, duration, spread and counts to reduce the severity of infections, to increase lung and sinus functions, reduce coughing, sneezing, inflammatory cytokines and toxins that effect the Vagus nerve, caused by viruses such as COVID-19 and flu in patients susceptible to these infections, including patients with hypoxemia, asthma, chronic obstructive pulmonary disease, cystic fibrosis, diabetics, long COVID, interstitial lung disease, pulmonary fibrosis, idiopathic pulmonary fibrosis, rhinitis medicamentosa also known as rebound rhinitis, allergic rhinitis, congestion, rebound effects of oxymetazoline, seasonal allergies, sinusitis, with migraines, Alzheimer's, Parkinsons and pulmonary hypertension which comprises:

contacting mammalian cells with a therapeutically effective amount of a composition, said composition including the following constituents:

a) sodium pyruvate;

b) sodium chloride;

c) benzalkonium chloride;

d) an alcohol selected from: ethanol, isopropanol, methyl alcohol or phenylethyl alcohol; and, e) an aqueous carrier;

wherein said composition contains the following amounts of said constituents: sodium pyruvate ranges from about 0.01% to 1%, sodium chloride ranges from 0.45% to 0.93%; benzalkonium chloride ranges from 0.01% to about 0.2% and alcohol ranges from 0.01% to about 0.2%, balance is said aqueous carrier, all percentages by weight.

11. The method of claim 10 wherein said sodium chloride ranges from 0.6% to 0.93% by weight, and is in a saline solution with said aqueous carrier.

12. The method of claim 10 wherein said benzalkonium chloride ranges from 0.04% to about 0.1% and alcohol ranges from 0.04% to about 0.1%, by weight.

13. The composition of claim 1 wherein said benzalkonium chloride content is about 0.06% and said alcohol content is about 0.06%, by weight.

14. The method of claim 10 wherein said composition contains the following amounts of said constituents: sodium chloride at about 0.9%; sodium pyruvate at about 0.21%, benzalkonium chloride at about 0.06% and alcohol at about 0.06%, all by weight.

15. The method of claim 10 wherein said method includes a step using an enhancing composition to enhance the efficacy of pulmonary drugs, steroids and cancer medications, where the enhancing composition is administered before and after said treatment that includes the composition set forth in the method of claim 10.

16. The method of claim 10 wherein said alcohol is ethanol and wherein said aqueous carrier is water selected from the group consisting of purified water and distilled water.

17. A method for delivering sodium pyruvate and other drugs through biofilms and mucus barriers to stimulate and increase the synthesis of nasal nitric oxide, that will reduce viral and bacterial replication, duration, spread and counts to reduce the severity of infections, to increase lung and sinus functions, reduce coughing, sneezing, inflammatory cytokines and toxins that effect the Vagus nerve, caused by viruses such as COVID-19 and flu in patients susceptible to these infections, including patients with hypoxemia, asthma, chronic obstructive pulmonary disease, cystic fibrosis, diabetics, long COVID, interstitial lung disease, pulmonary fibrosis, idiopathic pulmonary fibrosis, rhinitis medicamentosa also known as rebound rhinitis, allergic rhinitis, congestion, rebound effects of oxymetazoline, seasonal allergies, sinusitis, with migraines, Alzheimer's, Parkinsons and pulmonary hypertension which comprises:

contacting mammalian cells with a therapeutically effective amount of a composition, said composition including the following constituents:
  f) sodium pyruvate;
  g) sodium chloride;
  h) benzalkonium chloride;
  i) an alcohol selected from: ethanol, isopropanol, methyl alcohol or phenylethyl alcohol; and,
  j) an aqueous carrier;
wherein said composition contains the following amounts of said constituents: sodium pyruvate ranges from about 0.01% to 1%, sodium chloride ranges from 0.45% to 0.93%; benzalkonium chloride ranges from 0.01% to about 0.2% and alcohol ranges from 0.01% to about 0.2%, balance is said aqueous carrier, all percentages by weight; and,
wherein a therapeutic agent is administered relative to contacting said mammalian cells with said composition, and said therapeutic agent is administered at a time selected from the group consisting of: prior to, simultaneously with, and after, contacting said mammalian cells with said composition.

18. The method of claim 17 wherein said sodium chloride ranges from 0.6% to 0.93% by weight, and is in a saline solution with said aqueous carrier.

19. The method of claim 17 wherein said sodium chloride ranges from 0.6% to 0.93% by weight, and is in a saline solution with said aqueous carrier and wherein said aqueous carrier is water selected from the group consisting of purified water and distilled water.

20. The method of claim 17 wherein said benzalkonium chloride ranges from 0.04% to about 0.1% and alcohol ranges from 0.04% to about 0.1%, by weight.

* * * * *